(12) United States Patent
Ivosevic et al.

(10) Patent No.: US 11,712,691 B2
(45) Date of Patent: Aug. 1, 2023

(54) BIOLOGICAL FLUID SEPARATION DEVICE

(71) Applicant: Becton, Dickinson and Company, Franklin Lakes, NJ (US)

(72) Inventors: Milan Ivosevic, Kinnelon, NJ (US); Peng Li, Ridgewood, NJ (US); Scott Wentzell, Caldwell, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 266 days.

(21) Appl. No.: 16/612,577

(22) PCT Filed: Jun. 7, 2018

(86) PCT No.: PCT/US2018/036511
§ 371 (c)(1),
(2) Date: Nov. 11, 2019

(87) PCT Pub. No.: WO2018/226994
PCT Pub. Date: Dec. 13, 2018

(65) Prior Publication Data
US 2020/0197925 A1 Jun. 25, 2020

Related U.S. Application Data

(60) Provisional application No. 62/516,833, filed on Jun. 8, 2017.

(51) Int. Cl.
*B01L 3/00* (2006.01)
*G01N 33/49* (2006.01)
(52) U.S. Cl.
CPC ............ *B01L 3/502* (2013.01); *G01N 33/491* (2013.01); *B01L 2200/0668* (2013.01);
(Continued)

(58) Field of Classification Search
CPC ............. B01L 3/502; B01L 2200/0668; B01L 2300/042; B01L 2300/044;
(Continued)

(56) References Cited

U.S. PATENT DOCUMENTS

D239,021 S     3/1976  D'Alo
4,187,861 A *  2/1980  Heffernan ............. B01L 3/5082
                                                    422/913
(Continued)

FOREIGN PATENT DOCUMENTS

CN     1714292 A    12/2005
CN   102764133 A    11/2012
(Continued)

OTHER PUBLICATIONS

Doh et al., "Passive flow-rate regulators using pressure-dependent autonomous deflection of parallel membrane valves", Lab Chip, 2009, pp. 2070-2075, vol. 9, Royal Society of Chemistry, London, United Kingdom.
(Continued)

*Primary Examiner* — Matthew D Krcha
*Assistant Examiner* — Jacqueline Brazin
(74) *Attorney, Agent, or Firm* — The Webb Law Firm

(57) ABSTRACT

A biological fluid separation device and a separation process that allows for efficient separation of plasma from a blood sample is disclosed. A biological fluid separation device of the present disclosure is adapted to receive a blood sample having a cellular portion or cells and a plasma portion or plasma. A biological fluid separation device of the present disclosure separates plasma from cells using a track-etched membrane and cross-flow filtration.

19 Claims, 22 Drawing Sheets

(52) U.S. Cl.
CPC ... *B01L 2300/042* (2013.01); *B01L 2300/044* (2013.01); *B01L 2300/0681* (2013.01); *B01L 2300/0832* (2013.01); *B01L 2300/0877* (2013.01); *B01L 2300/0883* (2013.01); *B01L 2400/049* (2013.01)

(58) Field of Classification Search
CPC ..... B01L 2300/0681; B01L 2300/0832; B01L 2300/0877; B01L 2300/0883; B01L 2400/049; B01L 2200/0647; B01L 2300/0636; B01L 3/0296; G01N 33/491; A61B 5/15003; A61B 5/150351; A61B 5/150732; A61B 5/15074; A61B 5/150755; A61B 5/154
USPC ......................................................... 422/534
See application file for complete search history.

(56) References Cited

U.S. PATENT DOCUMENTS

| | | |
|---|---|---|
| 4,365,626 A | 12/1982 | House |
| 4,636,201 A | 1/1987 | Ambrose et al. |
| 4,832,695 A | 5/1989 | Rosenberg et al. |
| 4,929,232 A | 5/1990 | Sweeney et al. |
| 5,098,400 A | 3/1992 | Crouse et al. |
| D337,157 S | 7/1993 | Ortiz |
| 5,275,731 A | 1/1994 | Jahn |
| D375,788 S | 11/1996 | Potts et al. |
| D380,262 S | 6/1997 | Van Funderburk et al. |
| 5,647,849 A | 7/1997 | Kalin |
| D427,308 S | 6/2000 | Zinger |
| 6,382,254 B1 | 5/2002 | Yang et al. |
| 6,517,234 B1 | 2/2003 | Kopf-Sill et al. |
| 6,523,559 B2 | 2/2003 | Beebe et al. |
| D473,646 S | 4/2003 | Baillargeon et al. |
| 6,582,397 B2 | 6/2003 | Alesi et al. |
| D483,487 S | 12/2003 | Harding et al. |
| D486,225 S | 2/2004 | Gay, III |
| 6,743,399 B1 | 6/2004 | Weigl et al. |
| D492,774 S | 7/2004 | Cindrich et al. |
| D497,990 S | 11/2004 | Jutiia |
| D505,200 S | 5/2005 | Simpson et al. |
| 7,059,327 B2 | 6/2006 | Worthington |
| 7,097,811 B2 | 8/2006 | Yao et al. |
| 7,223,371 B2 | 5/2007 | Hayenga et al. |
| 7,293,581 B2 | 11/2007 | Gilbert et al. |
| 7,500,569 B2 * | 3/2009 | Manoussakis ....... G01N 33/491 422/550 |
| D605,755 S | 12/2009 | Baxter et al. |
| D607,558 S | 1/2010 | Abry et al. |
| 7,681,595 B2 | 3/2010 | Kim et al. |
| D629,510 S | 12/2010 | Grunhut |
| D633,199 S | 2/2011 | MacKay et al. |
| D637,713 S | 5/2011 | Nord et al. |
| D642,261 S | 7/2011 | York et al. |
| D655,000 S | 2/2012 | Mirigian |
| D655,017 S | 2/2012 | Mosler et al. |
| D679,008 S | 3/2013 | Schroeder et al. |
| D681,230 S | 4/2013 | Mosler et al. |
| D702,343 S | 4/2014 | Dale et al. |
| D702,835 S | 4/2014 | Vinchon |
| D709,753 S | 7/2014 | Guala |
| 8,858,507 B2 | 10/2014 | Nielsen et al. |
| D718,439 S | 11/2014 | Woehr et al. |
| D738,494 S | 9/2015 | Kashmirian |
| D750,239 S | 2/2016 | Pappalardo |
| D750,258 S | 2/2016 | Crossley |
| D750,779 S | 3/2016 | Ahluwalia et al. |
| D751,192 S | 3/2016 | She et al. |
| D755,966 S | 5/2016 | Ahluwalia et al. |
| D755,967 S | 5/2016 | Ahluwalia et al. |
| D757,258 S | 5/2016 | Weißhaupt et al. |
| D757,935 S | 5/2016 | Solingen et al. |
| D760,891 S | 7/2016 | Nakamura et al. |
| D761,422 S | 7/2016 | Row et al. |
| D765,241 S | 8/2016 | Holland |
| D768,850 S | 10/2016 | Rozwadowski et al. |
| D768,851 S | 10/2016 | Rozwadowski et al. |
| 2001/0044606 A1 | 11/2001 | Inkpen et al. |
| 2002/0153046 A1 | 10/2002 | Dantsker et al. |
| 2004/0133172 A1 | 7/2004 | Wilkinson |
| 2004/0210197 A1 | 10/2004 | Conway |
| 2006/0029923 A1 * | 2/2006 | Togawa .................. B01L 3/502 435/2 |
| 2006/0263873 A1 | 11/2006 | Levine et al. |
| 2007/0105156 A1 | 5/2007 | Togawa et al. |
| 2007/0129686 A1 | 6/2007 | Daily et al. |
| 2007/0134807 A1 | 6/2007 | Bao et al. |
| 2008/0017577 A1 | 1/2008 | Yi et al. |
| 2008/0160603 A1 | 7/2008 | Sundararajan et al. |
| 2008/0228147 A1 | 9/2008 | David-Hegerich et al. |
| 2009/0105661 A1 | 4/2009 | Chevallier et al. |
| 2009/0312705 A1 | 12/2009 | Grunhut et al. |
| 2011/0092915 A1 | 4/2011 | Olson et al. |
| 2012/0029439 A1 | 2/2012 | Hudson et al. |
| 2013/0085453 A1 | 4/2013 | Manke et al. |
| 2014/0042094 A1 | 2/2014 | Montagu et al. |
| 2014/0308165 A1 | 10/2014 | Marchiarullo et al. |
| 2014/0308179 A1 * | 10/2014 | Marchiarullo ... A61B 5/150305 422/527 |
| 2015/0045729 A1 | 2/2015 | Denzer et al. |
| 2015/0165129 A1 | 6/2015 | Row et al. |
| 2016/0129437 A1 * | 5/2016 | Kayyem ................. B01L 3/502 204/600 |
| 2016/0144132 A1 | 5/2016 | Scanlon |
| 2016/0193428 A1 | 7/2016 | Perthu |
| 2017/0014578 A1 | 1/2017 | Bunch |
| 2017/0157332 A1 | 6/2017 | Nguyen |
| 2017/0216835 A1 | 8/2017 | Ivosevic et al. |
| 2017/0354362 A1 | 12/2017 | Xu et al. |

FOREIGN PATENT DOCUMENTS

| | | | |
|---|---|---|---|
| CN | 106604780 A | 4/2017 | |
| EP | 2886144 A1 | 6/2015 | |
| JP | H11-235330 A | 8/1999 | |
| JP | 2002-125955 A | 5/2002 | |
| JP | 2007000536 | * 1/2007 | |
| JP | 2007000536 A | 1/2007 | |
| JP | 2008245778 A | 10/2008 | |
| JP | 2009-028079 A | 2/2009 | |
| JP | 2016-518922 A | 6/2016 | |
| WO | WO-8701048 A1 * | 2/1987 | .............. F04B 17/04 |
| WO | 9614578 A1 | 5/1996 | |
| WO | 03051423 A2 | 6/2003 | |
| WO | 2010142812 A1 | 12/2010 | |
| WO | 2011114917 A1 | 9/2011 | |
| WO | 2014143815 A2 | 9/2014 | |
| WO | 2014150201 A1 | 9/2014 | |
| WO | 2014164943 A1 | 10/2014 | |
| WO | 2015105511 A1 | 7/2015 | |
| WO | 2015123096 A1 | 8/2015 | |

OTHER PUBLICATIONS

Jeong et al., "Siphon-driven microfluidic passive pump with a yarn flow resistance controller", Lab Chip, 2014, pp. 4213-4219, vol. 14, Royal Society of Chemistry, London, United Kingdom.

Kim et al., "Modulation of fluidic resistance and capacitance for long-term, high-speed feedback control of a microfluidic interface", Lab Chip, 2009, pp. 2603-2609, vol. 9, Royal Society of Chemistry, London, United Kingdom.

Oh et al., "Design of pressure-driven microfluidic networks using electric circuit analogy", Lap Chip, 2012, pp. 515-545, vol. 12, Royal Society of Chemistry, London, United Kingdom.

Wang et al., "Simple filter microchip for rapid separation of plasma and viruses from whole blood", International Journal of Nanomedicine,

(56) References Cited

OTHER PUBLICATIONS 2012, pp. 5019-5028, vol. 7, Dove Medical Press Ltd., Macclesfield, United Kingdom.

* cited by examiner

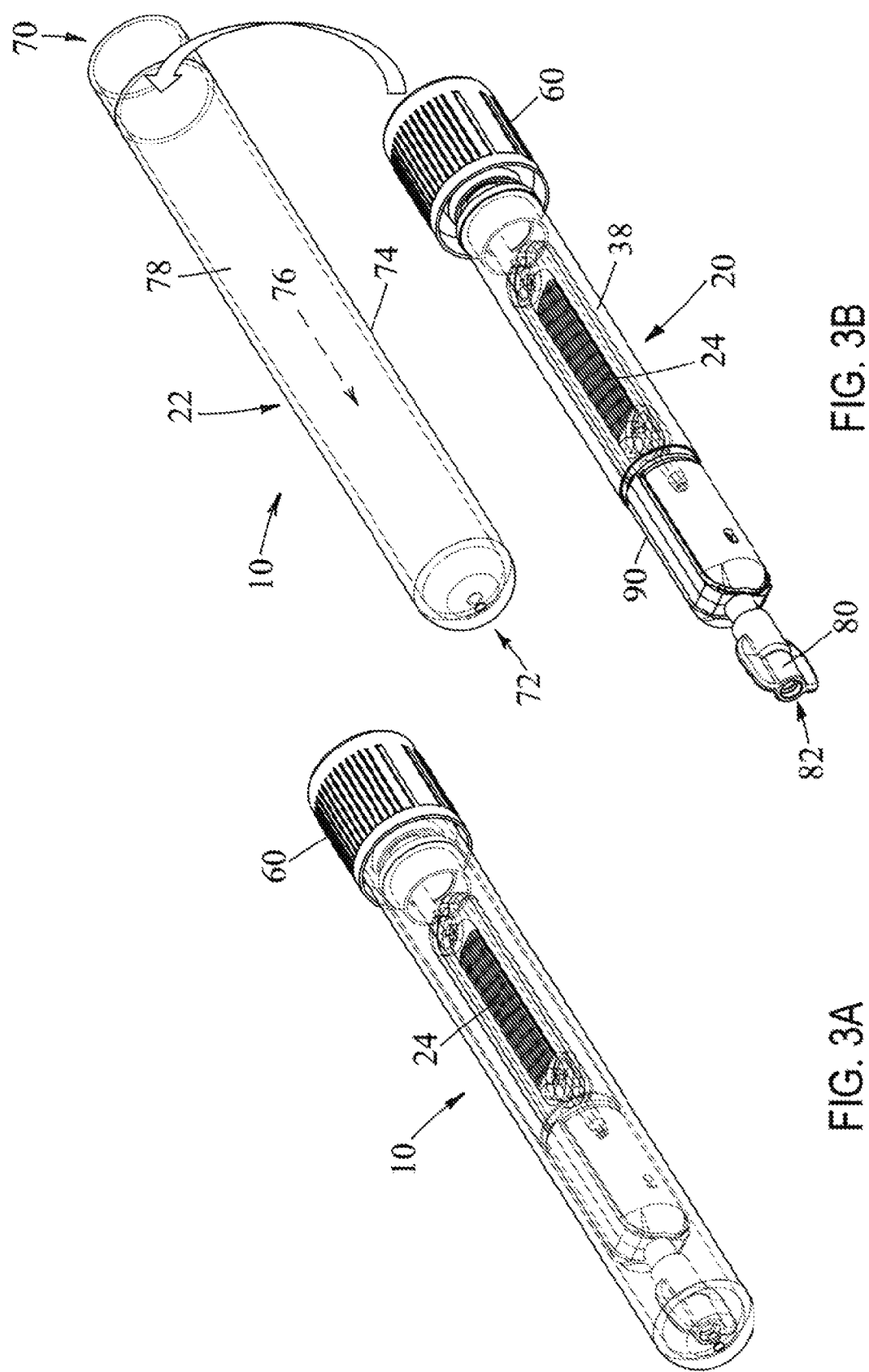

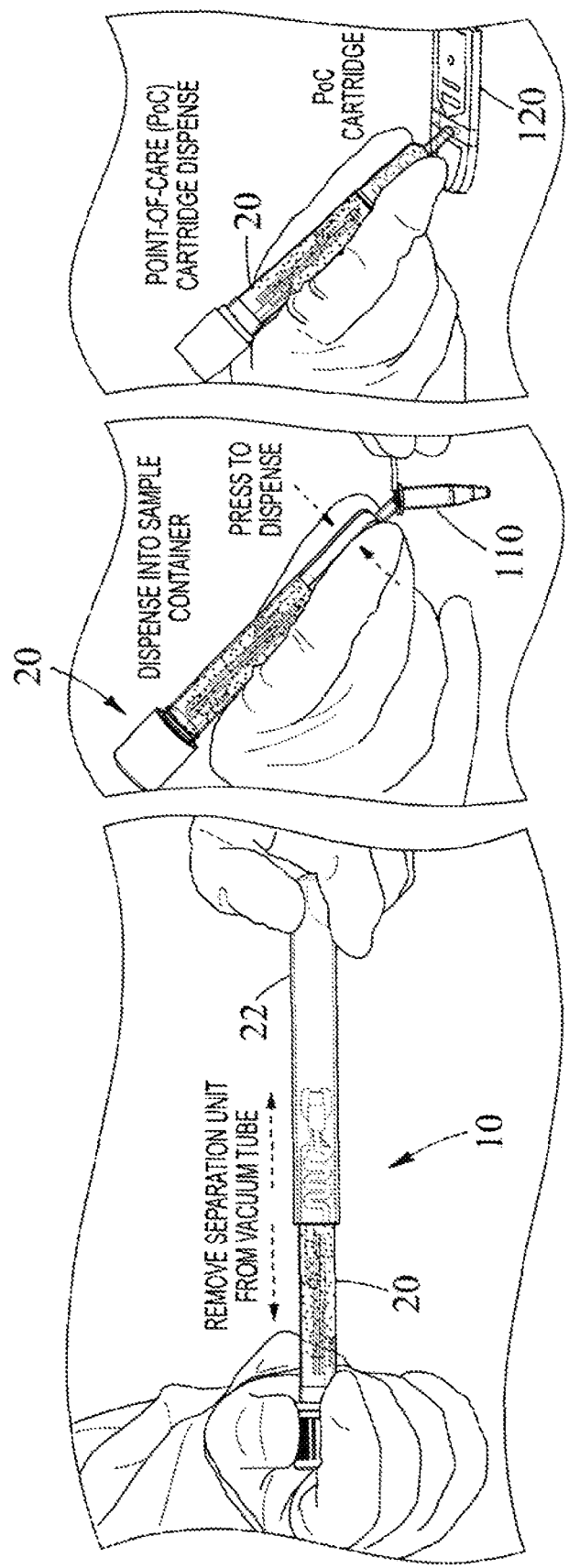

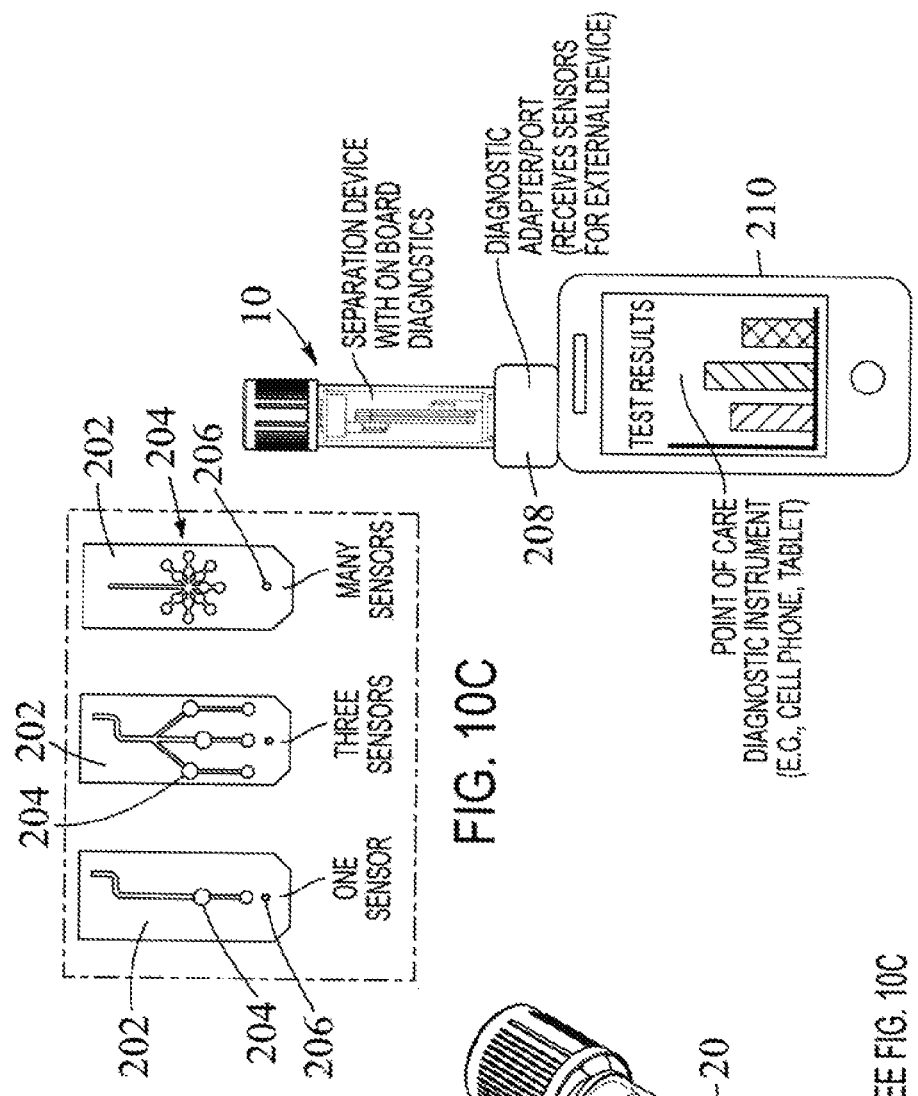

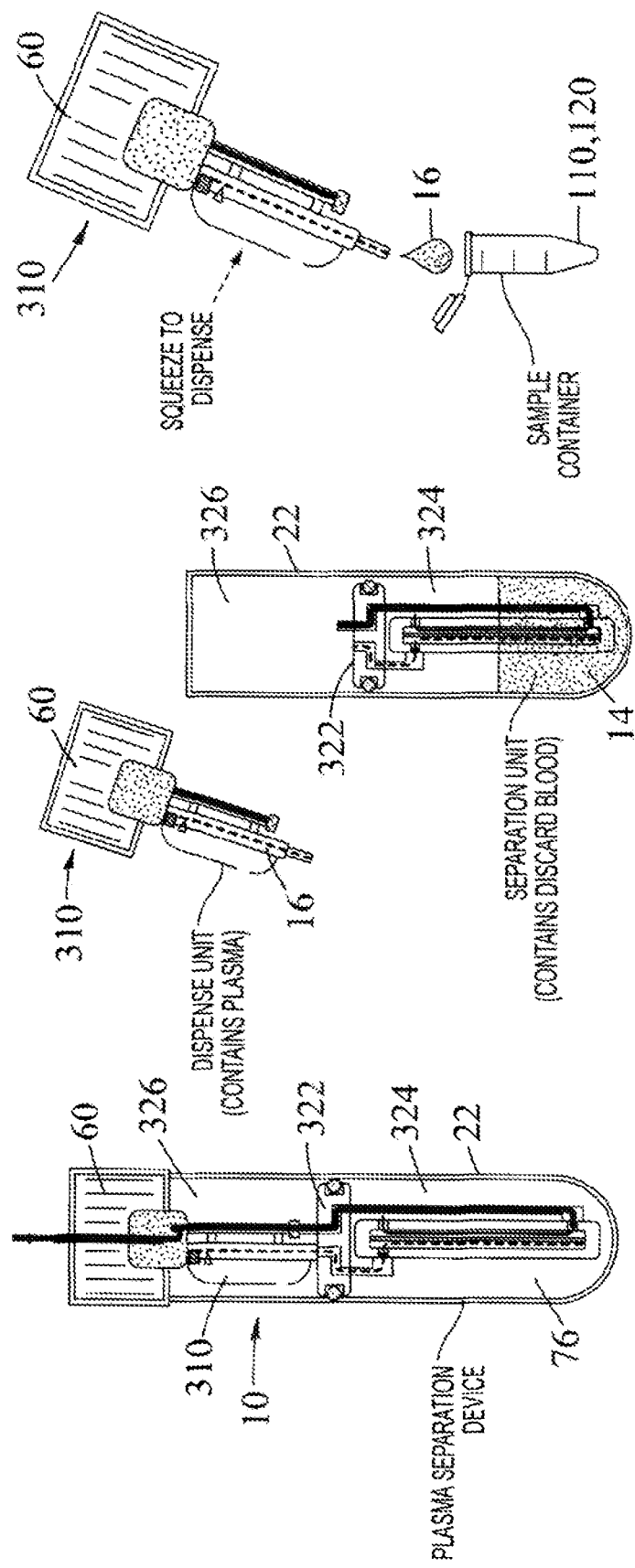

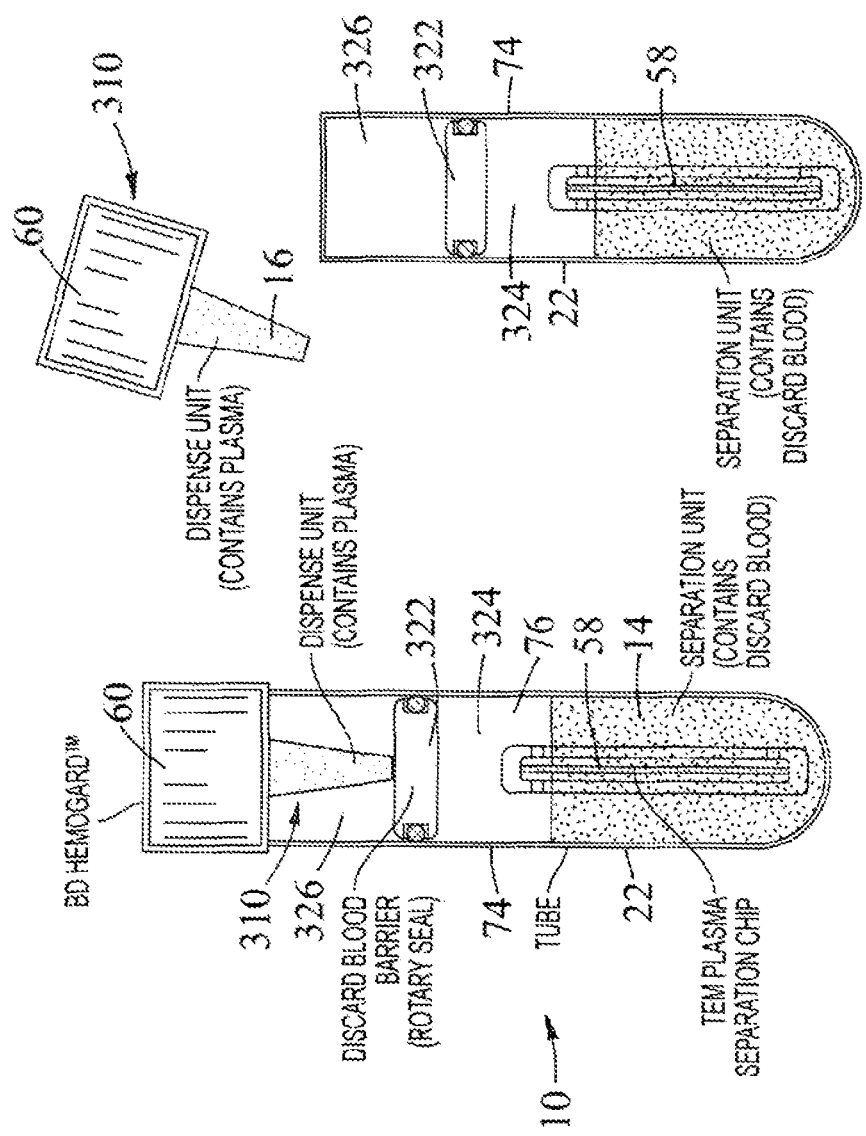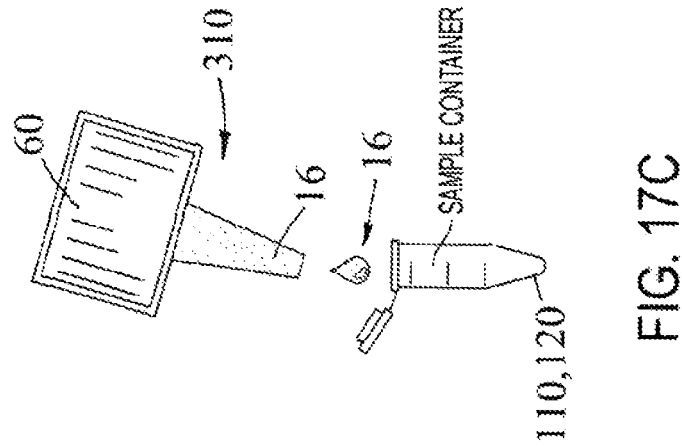

BIOLOGICAL FLUID SEPARATION DEVICE

CROSS-REFERENCE TO RELATED APPLICATIONS

This application is the United States national phase of International Application No. PCT/US2018/036511 filed Jun. 7, 2018, and claims priority to U.S. Provisional Patent Application No. 62/516,833 filed Jun. 8, 2017, the disclosures of which are hereby incorporated by reference in their entirety.

BACKGROUND OF THE INVENTION

1. Field of the Disclosure

The present disclosure relates generally to devices adapted for use with biological fluids. More particularly, the present disclosure relates to devices adapted for separating components of biological fluids.

2. Description of the Related Art

Blood sampling is a common health care procedure involving the withdrawal of at least a drop of blood from a patient. Blood samples are commonly taken from hospitalized, homecare, and emergency room patients either by finger stick, heel stick, or venipuncture. Blood samples may also be taken from patients by venous or arterial lines. Once collected, blood samples may be analyzed to obtain medically useful information including chemical composition, hematology, or coagulation, for example.

Blood tests determine the physiological and biochemical states of the patient, such as disease, mineral content, drug effectiveness, and organ function. Blood tests may be performed in a clinical laboratory or at the point-of-care near the patient. One example of point-of-care blood testing is the routine testing of a patient's blood glucose levels which involves the extraction of blood via a finger stick and the mechanical collection of blood into a diagnostic cartridge. Thereafter, the diagnostic cartridge analyzes the blood sample and provides the clinician a reading of the patient's blood glucose level. Other devices are available which analyze blood gas electrolyte levels, lithium levels, and ionized calcium levels. Some other point-of-care devices identify markers for acute coronary syndrome (ACS) and deep vein thrombosis/pulmonary embolism (DVT/PE).

Blood samples contain a cellular portion, blood cells, and a plasma portion, blood plasma. Core lab tests comprise the bulk of blood testing, and use centrifugation to separate blood plasma from blood cells for analysis in a lab before the tubes are presented to large diagnostic instruments. Centrifugation is the commonly accepted process for plasma separation for general use across many laboratory tests. Centrifugation typically takes 15 to 20 minutes and involves heavy labor or complex work flow.

In a point-of-care environment, blood samples are presented to the instrument at or near the patient bedside. Most point-of-care tests use whole blood samples that are transferred from a blood collection tube by pipette or syringe, because plasma samples are not available at the patient's bedside.

SUMMARY OF THE INVENTION

The present disclosure provides a biological fluid separation device and a separation process that allows for efficient separation of plasma from a blood sample. A biological fluid separation device of the present disclosure is adapted to receive a blood sample having a cellular portion or cells and a plasma portion or plasma. A biological fluid separation device of the present disclosure separates plasma from cells using a track-etched membrane and cross-flow filtration.

In one embodiment, a biological fluid separation device of the present disclosure provides a plasma separation device integrated within an evacuated blood collection tube. Advantageously, a biological fluid separation device of the present disclosure provides for the immediate separation of plasma during clinical blood draws and the ability for controlled dispense of the separated plasma sample to a point-of-care cartridge or other diagnostic instrument port or testing device. A biological fluid separation device of the present disclosure provides a blood collection workflow that is no different than a conventional blood collection workflow using vacuum tubes such as the BD Vacutainer® and corresponding venous access sets. A biological fluid separation device of the present disclosure generates plasma that is immediately available for controlled dispense to a diagnostic instrument at the point-of-care or in a near-patient diagnostic setup.

A biological fluid separation device of the present disclosure allows for immediate plasma separation during the blood draw therefore eliminating the need for a separate centrifugation process and also allows controlled plasma sample transfer to a diagnostic port using the embedded precise drop dispenser of the present disclosure. A biological fluid separation device of the present disclosure eliminates the need for conventional blood collection tubes to be centrifuged, which often requires being sent to the lab for centrifugation.

In accordance with an embodiment of the present invention, a biological fluid separation device is adapted to receive a blood sample having a first portion and a second portion. The biological fluid separation device includes a housing having an inlet and an outlet and a venting plug, and a blood chamber having a blood chamber inlet and a blood chamber outlet, with the blood chamber adapted to receive the blood sample. The biological fluid separation device further includes a separated chamber having a chamber outlet, and a separator disposed between the blood chamber and the separated chamber, with the separator adapted to trap the first portion in the blood chamber and allow the second portion to pass through the separator into the separated chamber. The biological fluid separation device further includes an outer housing removably connectable to the housing, wherein the outer housing contains a first vacuum and the housing contains a second vacuum, and with the housing connected to the outer housing, the housing is disposed within the outer housing. The first vacuum and the second vacuum are in communication via the venting plug.

In one configuration, the first portion is a cellular portion, and the second portion is a plasma portion. The first vacuum and the second vacuum may draw the blood sample within the housing and draw the plasma portion through the separator into the separated chamber.

In certain configurations, the separator may include a membrane surface having pores. Optionally, the separator is a track-etched membrane.

The biological fluid separation device may also include a closure covering the inlet, and, with the housing connected to the outer housing, the closure may seal the open end of the housing. The inlet of the housing may be provide at a first end and the outlet of the housing may be provided at an opposite second end.

In other configurations, the biological fluid separation device may also include a plasma collection channel between the chamber outlet and the outlet of the housing. Optionally, the plasma collection channel may have a serpentine shape.

In still other configurations, the biological fluid separation device may further include a dispenser assembly which includes a cap covering the outlet and including the venting plug which allows air to pass therethrough and prevents the second portion of the blood sample from passing therethrough. The dispenser assembly may also include a deformable portion transitionable between an initial position in which the second portion is contained within the separated chamber and a deformed position in which a portion of the second portion is expelled from the separated chamber. With the cap removed from the outlet, and the deformable portion transitioned to the deformed position, a portion of the second portion may expelled from the biological fluid separation device.

In still further configurations, the biological fluid separation device may include a diagnostic assembly which includes a diagnostic interface in communication with the chamber outlet of the separated chamber, and a sensor for testing the second portion.

In accordance with another embodiment of the present invention a biological fluid separation device adapted to receive a blood sample having a cellular portion and a plasma portion, may include an inner housing having an inlet and an outlet. The biological fluid separation device may also include a blood chamber having a blood chamber inlet and a blood chamber outlet, wherein the blood chamber receives the blood sample, and a plasma chamber having a plasma chamber outlet. The biological fluid separation device may also include a separator disposed between the blood chamber and the plasma chamber, with the separator adapted to trap the cellular portion in the blood chamber and allow the plasma portion to pass through the separator into the plasma chamber, and an outer housing removably connectable to the inner housing. With the inner housing connected to the outer housing, the inner housing may be disposed within the outer housing, and wherein a vacuum is defined by at least one of the inner housing and the outer housing to draw the plasma portion of the blood sample through the separator.

The biological fluid separation device may further include a biological fluid separation device connector removably connectable to a connector of a blood collection tube. Optionally, the outer housing of the biological fluid separation device may include an evacuated tube.

In accordance with still another embodiment of the present invention, a biological fluid separation device may be adapted to receive a blood sample having a cellular portion and a plasma portion. The biological fluid separation device may include an outer housing having an open end, a closed end, and a sidewall extending therebetween and defining an interior. The biological fluid separation device may further include a dispenser unit removably connectable to the outer housing, and an inner housing within the outer housing. The inner housing may include a blood chamber having a blood chamber inlet and a blood chamber outlet, the blood chamber configured to receive the blood sample and the blood chamber outlet in fluid communication with a portion of the interior of the outer housing. The biological fluid separation device further including a plasma chamber having a plasma chamber outlet, and a separator disposed between the blood chamber and the plasma chamber. The separator may be adapted to trap the cellular portion in the blood chamber and allow the plasma portion to pass through the separator into the plasma chamber. The biological fluid separation device further including a plasma collection channel extending from the plasma chamber outlet into the dispenser unit.

Optionally, the biological fluid separation device may also include a stopper sized relative to the interior of the outer housing to provide sealing engagement with the sidewall of the outer housing. The stopper may divide the interior of the outer housing into a first sealed portion and a second portion. In certain configurations, with the dispenser unit disconnected from the outer housing, the plasma portion is contained within the dispenser unit.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein:

FIG. 3A is a perspective view of a biological fluid separation device in accordance with an embodiment of the present invention.

FIG. 3B is an exploded, perspective view of a biological fluid separation device in accordance with an embodiment of the present invention.

FIG. 4C is a perspective view of a third step of using a biological fluid separation device of the present disclosure in accordance with an embodiment of the present invention.

FIG. 4D is a perspective view of a dispensing step of using a biological fluid separation device of the present disclosure in accordance with an embodiment of the present invention.

FIG. 4E is a perspective view of a dispensing step of using a biological fluid separation device of the present disclosure in accordance with an embodiment of the present invention.

FIG. 10A is a perspective view of a first step of using a biological fluid separation device of the present disclosure in accordance with another embodiment of the present invention.

FIG. 10B is a perspective view of a second step of using a biological fluid separation device of the present disclosure in accordance with another embodiment of the present invention.

FIG. 10C is an enlarged view of different sensor configurations of FIG. 10B in accordance with another embodiment of the present invention.

FIG. 10D is a perspective view of a third step of using a biological fluid separation device of the present disclosure in accordance with another embodiment of the present invention.

FIG. 16A is a perspective view of a first step of using a biological fluid separation device of the present disclosure in accordance with another embodiment of the present invention.

FIG. 16B is a perspective view of a second step of using a biological fluid separation device of the present disclosure in accordance with another embodiment of the present invention.

FIG. 16C is a perspective view of a third step of using a biological fluid separation device of the present disclosure in accordance with another embodiment of the present invention.

FIG. 17A is a perspective view of a first step of using a biological fluid separation device of the present disclosure in accordance with another embodiment of the present invention.

FIG. 17B is a perspective view of a second step of using a biological fluid separation device of the present disclosure in accordance with another embodiment of the present invention.

FIG. 17C is a perspective view of a third step of using a biological fluid separation device of the present disclosure in accordance with another embodiment of the present invention.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION

Figure 1:
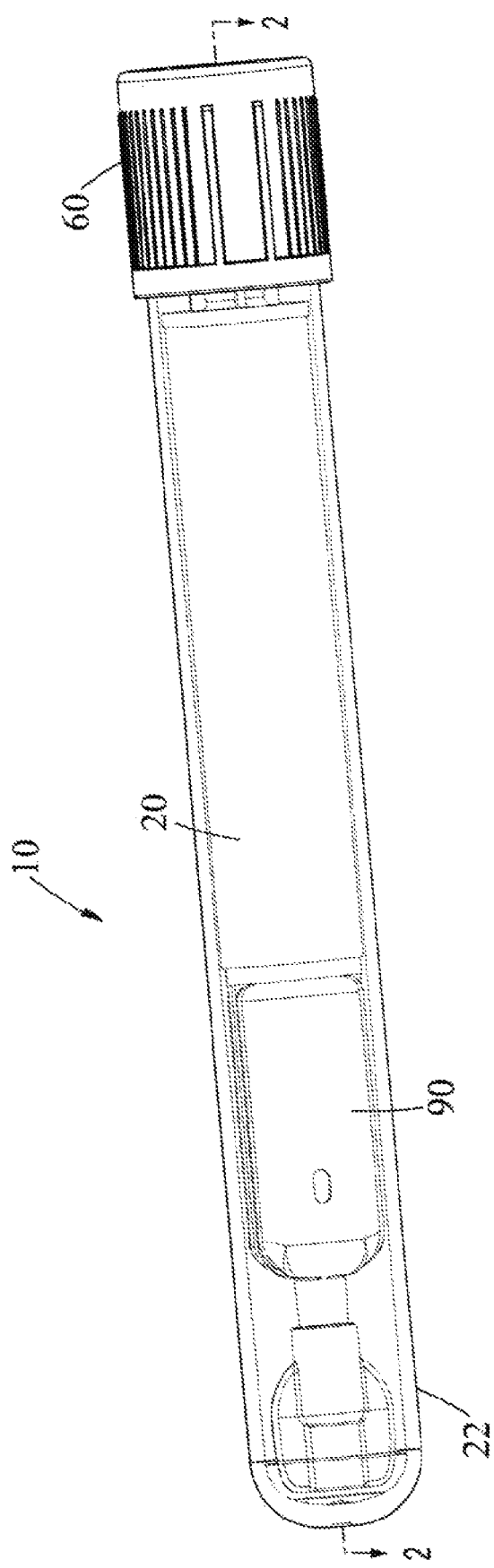
FIG. 1 is a perspective view of a biological fluid separation device in accordance with an embodiment of the present invention.
Figure 2:
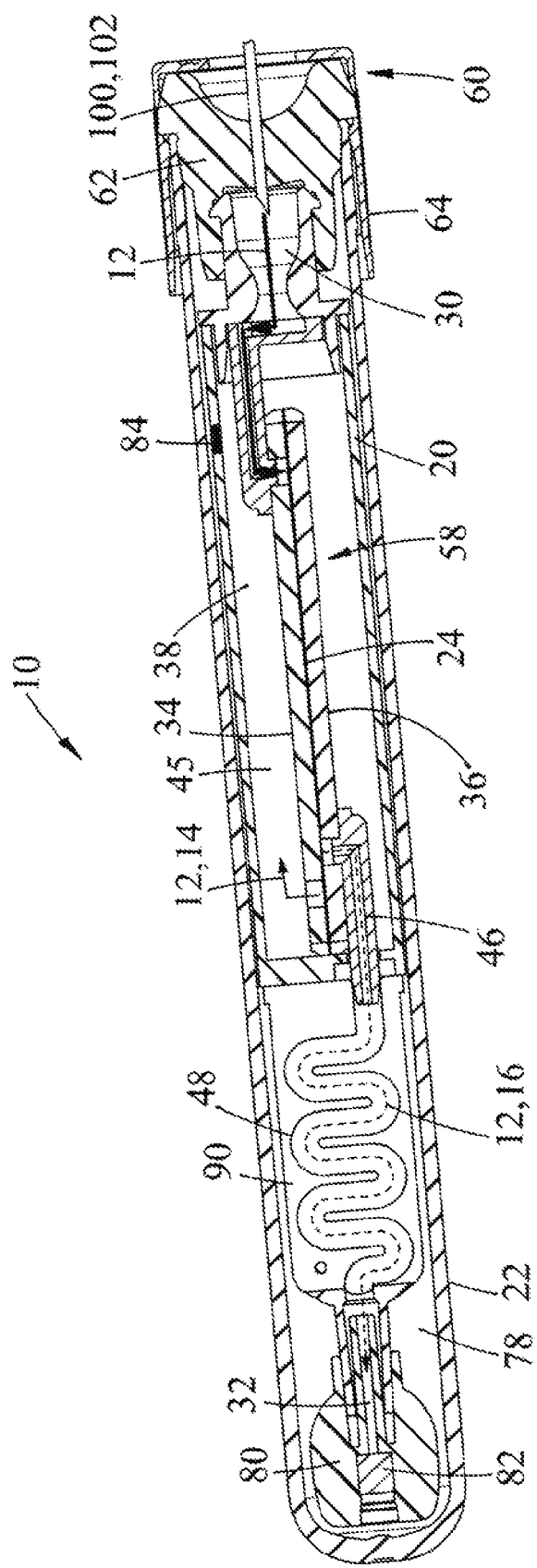
FIG. 2 is a cross-sectional view taken along line 2-2 of FIG. 1 in accordance with an embodiment of the present invention.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume alternative variations and step sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting.

FIGS. 1-4E illustrate an exemplary embodiment of a biological fluid separation device of the present disclosure. Referring to FIGS. 1-4E, a biological fluid separation device 10 of the present disclosure is adapted to receive a blood sample 12 having a first portion, such as a cellular portion 14 and a second portion, such as a plasma portion 16. The present disclosure provides a biological fluid separation device and a separation process that allows for efficient separation of plasma from a blood sample.

In one embodiment, a biological fluid separation device of the present disclosure provides a plasma separation device integrated within an evacuated blood collection tube. Advantageously, a biological fluid separation device of the present disclosure provides for the immediate separation of plasma during clinical blood draws and the ability for controlled dispense of the separated plasma sample to a point of care cartridge or other diagnostic instrument port or testing device. A biological fluid separation device of the present disclosure provides a blood collection workflow that is no different than a conventional blood collection workflow using vacuum tubes such as the BD Vacutainer® and corresponding venous access sets. A biological fluid separation device of the present disclosure generates plasma that is immediately available for controlled dispense to a diagnostic instrument at the point of care or in a near-patient diagnostic setup.

A biological fluid separation device of the present disclosure allows for immediate plasma separation during the blood draw therefore eliminating the need for a separate centrifugation process and also allows controlled plasma sample transfer to a diagnostic port using the embedded precise drop dispenser of the present disclosure. A biological fluid separation device of the present disclosure eliminates the need for conventional blood collection tubes to be centrifuged, which often requires being sent to the lab for centrifugation.

Referring to FIGS. 1-4E, in one exemplary embodiment, a biological fluid separation device 10 generally includes an inner housing or internal tube 20, an outer housing or external tube 22, and a separator 24.

Referring to FIGS. 1-4E, the inner housing 20 includes an inlet 30, an outlet 32, a blood chamber 34 that receives the blood sample 12, a separated chamber, such as a plasma chamber 36, and the separator 24. In one embodiment, the inlet 30 of the inner housing 20 is at a first end and the outlet 32 of the inner housing 20 is at an opposite second end. In other embodiments, the configuration of the inlet 30 and the outlet 32 may be varied for different applications.

Referring to FIGS. 1-4E, the blood chamber 34 receives the blood sample 12 and includes a blood chamber inlet 40, a blood chamber outlet 42, and a blood chamber channel 44 running between the blood chamber inlet 40 and the blood chamber outlet 42. In one embodiment, the blood chamber inlet 40 is in fluid communication with the inlet 30 of the biological fluid separation device 10. In one embodiment, the blood chamber 34 also includes a blood discard chamber 45 that is in fluid communication with the blood chamber outlet 42. In this manner, the cellular portion 14 of the blood sample 12 can be moved and stored within the blood discard chamber 45 after flowing through the blood chamber channel 44 and past the separator 24. The plasma chamber 36 includes a plasma chamber outlet 46.

Referring to FIGS. 1-4E, the separator 24 is disposed between the blood chamber 34 and the plasma chamber 36. In one embodiment, the separator 24 is adapted to trap the cellular portion 14 of the blood sample 12 in the blood chamber 34 and allow the plasma portion 16 of the blood sample 12 to pass through the separator 24 into the plasma chamber 36.

Figure 3C:
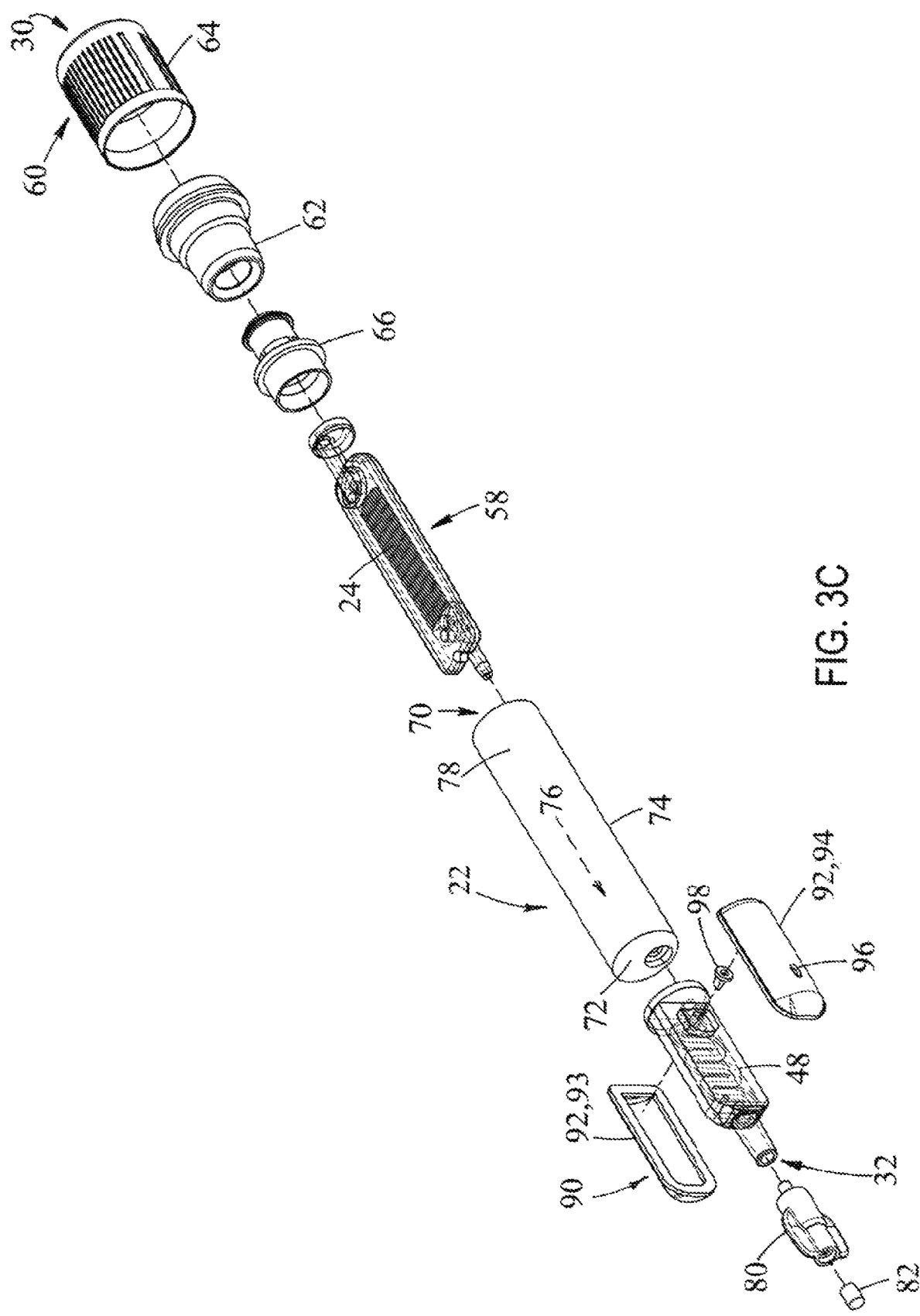
FIG. 3C is an exploded, perspective view of a biological fluid separation device in accordance with an embodiment of the present invention.
Figure 3D:
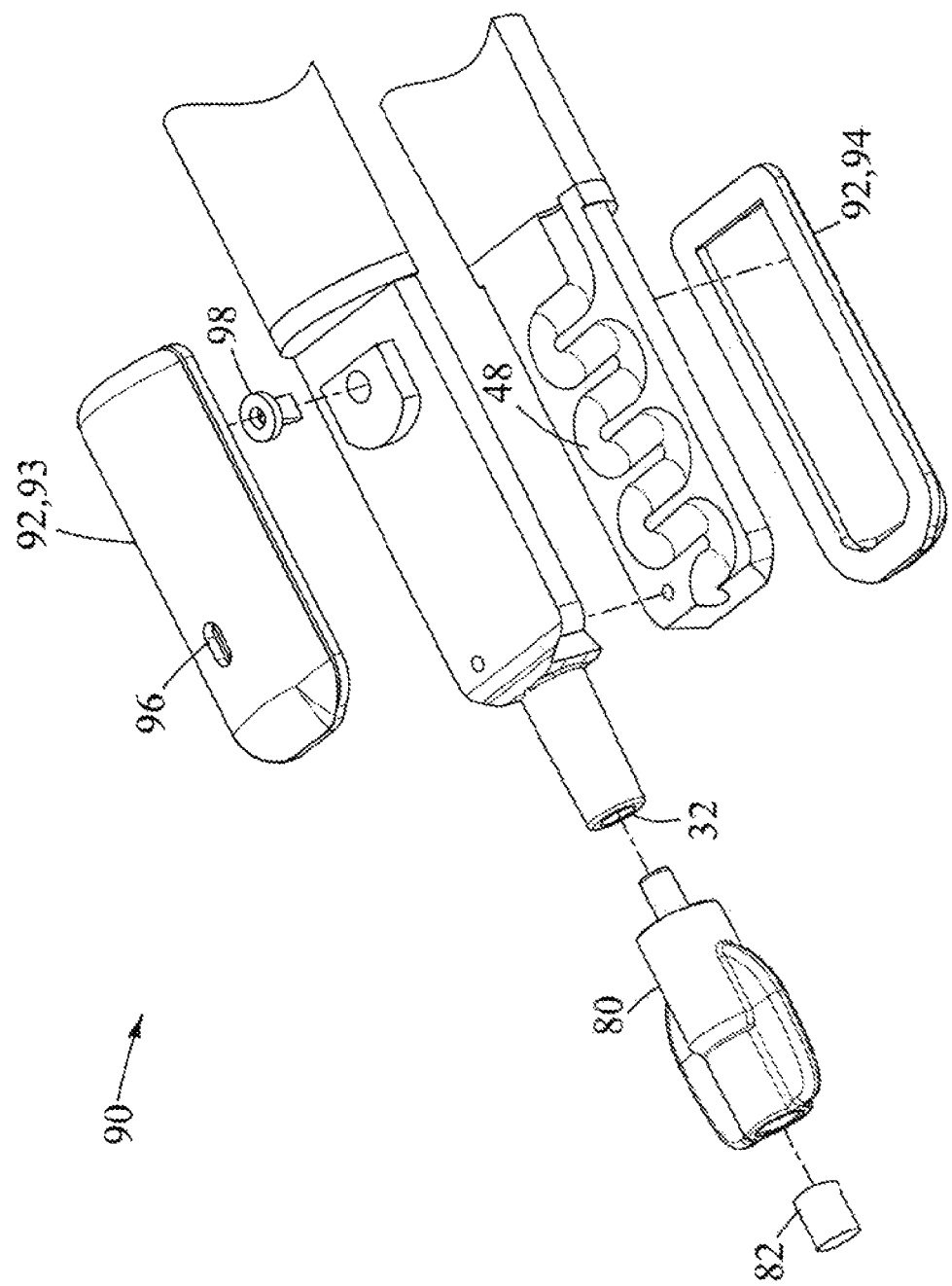
FIG. 3D is an exploded, perspective view of a dispenser assembly of a biological fluid separation device in accordance with an embodiment of the present invention.

In one embodiment, the separator 24 includes a membrane surface 50 having pores or filter holes 52. The membrane surface 50 has a first or blood side 54 and a second or plasma side 56. Referring to FIG. 3E, the blood chamber channel 44 is parallel to the membrane surface 50 as discussed in more detail below.

In one embodiment, the separator 24 comprises a track-etched membrane. The biological fluid separation device 10 of the present disclosure separates plasma 16 from cells 14 using a track-etched membrane and cross-flow filtration. A track-etched membrane of the biological fluid separation device 10 is a filter with pores small enough to prevent the flow of red blood cells or cells but permit the flow of plasma therethrough. Plasma flow through the membrane is driven by a pressure across the membrane, i.e., a transmembrane pressure, but this flow also brings cells to the membrane surface and risks membrane clogging. This is prevented by continuous blood flow parallel to the membrane surface, i.e., cross-flow filtration, which flushes cells away and allows continuous plasma filtration.

Figure 3F:
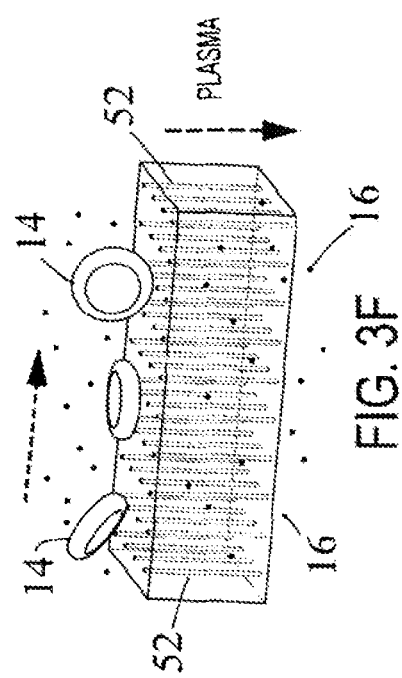
FIG. 3F is an enlarged partial cross-sectional view of a separator of a biological fluid separation device in accordance with an embodiment of the present invention.
Figure 3G:
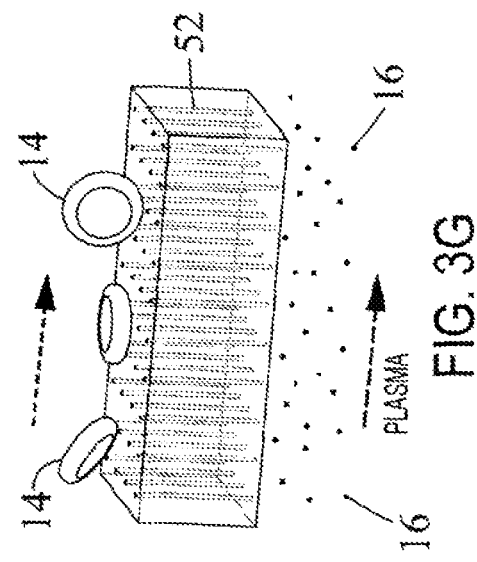
FIG. 3G is an enlarged partial cross-sectional view of a separator of a biological fluid separation device in accordance with an embodiment of the present invention.
Figure 3E:
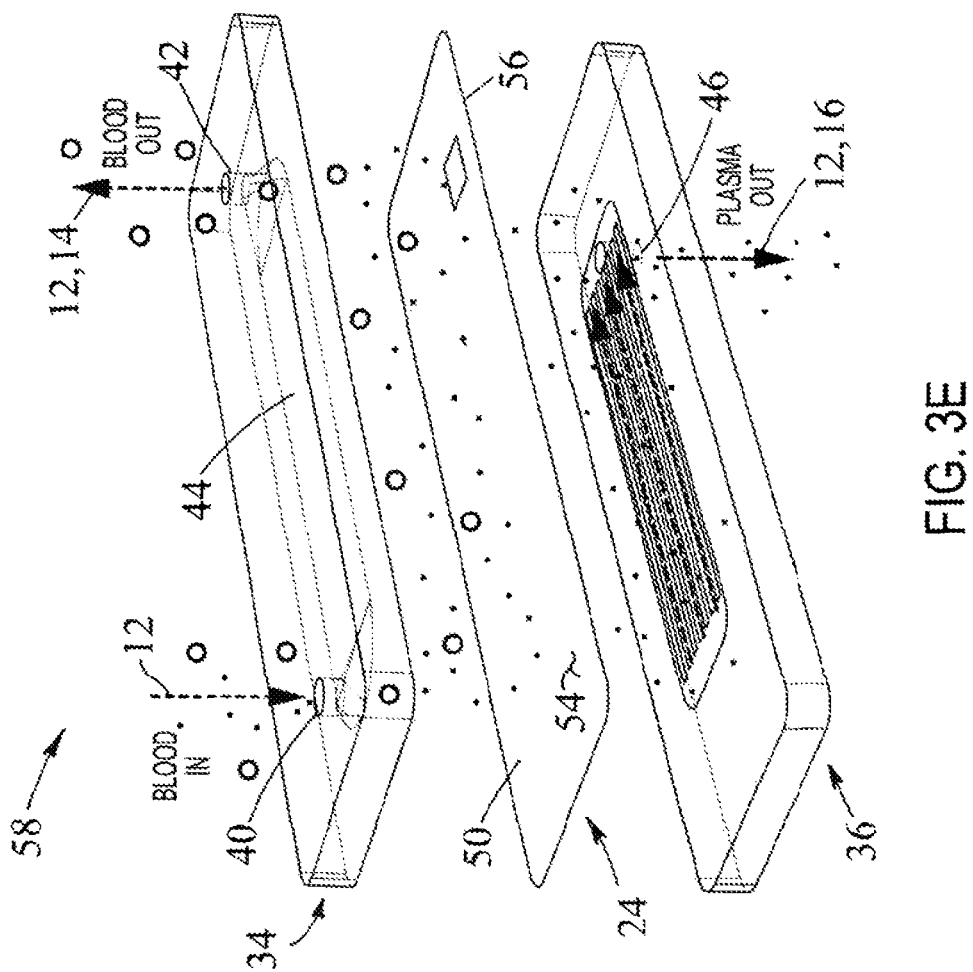
FIG. 3E is an exploded, perspective view of a separator chip of a biological fluid separation device in accordance with an embodiment of the present invention.

In one embodiment, the biological fluid separation device 10 of the present disclosure controls the blood flow rate on one side, i.e., a first or blood side 54, of a track-etched membrane while the differential pressure across the track-etched membrane extracts plasma 16 to the other side, i.e., a second or plasma side 56, of the track-etched membrane, as shown in FIGS. 3E and 3F. A blood sample 12 that falls into the blood chamber 34 flows within the blood chamber channel 44 parallel to the membrane surface 50 of the separator 24. In this manner, such parallel flow keeps cells 14 of the blood sample 12 from clogging the pores 52 of the separator 24, whose submicron pores 52 allow the flow of plasma 16 to other side, i.e., the plasma side 56, and further out into the plasma chamber 36.

In one embodiment, the separator 24 comprises a track-etched membrane with submicron holes 52 to filter plasma 16 from a blood sample 12 that is continuously flowing parallel to the membrane surface 50. In this manner, clogging of the filter holes 52 is prevented, as shown in FIG. 3F. Advantageously, the separation process of the present disclosure does not continuously trap the cells inside the filter structure, eventually reducing the yield to zero.

A biological fluid separation device 10 of the present disclosure is designed to effectively separate blood cells from the plasma without damaging the cells, e.g., cell rupture known as hemolysis. A biological fluid separation device 10 of the present disclosure balances fundamental blood flow characteristics in a way to maximize the plasma yield within a given time while preserving the cell integrity. In some embodiments, a biological fluid separation device 10 of the present disclosure is designed using mathematically modeling, e.g., using an equivalent electric circuit method, each portion of the filtration system to determine critical flow and geometric parameters that will maximize yield, minimize separation time, and minimize hemolysis.

In one embodiment, the separator 24 comprises a less than 100 microns thick track-etched membrane. In one embodiment, the separator 24 comprises a 5-25 micron thick track-etched membrane. In another embodiment, the separator 24 comprises a 6-14 micron thick track-etched membrane.

In one embodiment, the submicron holes 52 of the track-etched membrane are approximately 0.1-1.0 microns in diameter. In another embodiment, the submicron holes 52 of the track-etched membrane are approximately 0.2-0.8 microns in diameter.

In one embodiment, the active filter surface area of the track-etched membrane is less than 40 $mm^2$ Advantageously, this allows the separator 24 of the present disclosure to fit inside of conventional blood collection tubes and also generate high quality plasma with minimal analyte bias, and especially low bias of cardiac markers such as Troponin and BNP.

Referring to FIG. 3E, in one embodiment, the separator 24, the blood chamber 34, and the plasma chamber 36 form a separator chip 58. In one embodiment, the separator chip 58 is sized to be contained within the inner housing 20.

In one embodiment, the separator chip 58 has a chip length of approximately 9-125 mm. In one embodiment, the separator chip 58 has a chip width of approximately 8-16 mm. In one embodiment, the separator chip 58 has a chip thickness of approximately 0.5-2 mm.

In one embodiment, the height of the blood chamber 34 is approximately 30-200 microns. In one embodiment, the length of the blood chamber 34 is approximately 5-121 microns. In one embodiment, the height of the plasma chamber 36 is approximately 60-1000 microns.

In one embodiment, the biological fluid separation device 10 of the present disclosure includes an outer housing 22 that is removably connectable to the inner housing 20. Referring to FIGS. 1-3A, with the inner housing 20 connected to the outer housing 22, the inner housing 20 is disposed within the outer housing 22. The outer housing 22 includes an open end 70, a closed end 72, and a sidewall 74 extending therebetween and defining an interior 76. In one embodiment, the outer housing 22 contains a first vacuum 78.

Referring to FIGS. 1-3C, in one embodiment, the biological fluid separation device 10 includes a closure 60 that covers the inlet 30. Referring to FIGS. 1-3C, the closure 60 is engaged with the inlet 30 to seal the biological fluid separation device 10. The closure 60 protectively covers the inlet 30. The closure 60 allows for introduction of a blood sample 12 into the blood chamber 34 of the inner housing 20 and may include a pierceable self-sealing stopper 62 with an outer shield 64 such as a Hemogard™ cap commercially available from Becton, Dickinson and Company. In one embodiment, the closure 60 includes a stopper adapter 66.

Referring to FIGS. 1-3C, in one embodiment, the outer housing 22 is removably connectable to the inner housing 20 via the closure 60. For example, the closure 60 secures to the outer housing 22. In this manner, with the inner housing 20 connected to the outer housing 22, the closure 60 seals the open end 70 of the outer housing 22.

In one embodiment, the outer housing 22 is an evacuated tube. In one embodiment, the outer housing 22 may be a vacuum containing blood collection tube such as a Vacutainer® blood collection tube commercially available from Becton, Dickinson and Company.

Referring to FIGS. 1-3C, in one embodiment, the inner housing 20 includes a cap 80 that is removably attachable to the outlet 32 and that protectively covers the outlet 32. In one embodiment, the cap 80 includes a venting plug 82 which allows air to pass therethrough and prevents the plasma 16 of the sample 12 from passing therethrough.

The construction of the cap 80 and venting plug 82 allows air to pass through the cap 80 while preventing the plasma 16 of the blood sample 12 from passing through the cap 80 and may include a hydrophobic filter. The venting plug 82 has selected air passing resistance that may be used to finely control the filling rate of the blood chamber 34 and/or the plasma chamber 36 of the inner housing 20. By varying the porosity of the plug 82, the velocity of the air flow out of the cap 80, and thus the velocity of the blood sample flow into the inner housing 20, may be controlled.

Referring to FIGS. 1-3C, in one embodiment, the outer housing 22 contains a first vacuum 78 and the inner housing 20 contains a second vacuum 38. In one embodiment, the first vacuum 78 and the second vacuum 38 are in communication via the venting plug 82. In other embodiments, the inner housing 20 may also include a second venting plug and/or a venting plug valve 84 that allow the first vacuum 78 and the second vacuum 38 to be in communication theretogether.

The first vacuum 78 and the second vacuum 38 draw a blood sample 12 within the inner housing 20 and draw the plasma portion 16 through the separator 24 into the plasma chamber 36, as described in more detail below.

In one embodiment, the venting plug 82 of the cap 80, which allows air to pass therethrough and prevents the plasma 16 of the sample 12 from passing therethrough, seals the plasma chamber 36 once plasma 16 wets out the venting plug 82 and ends separation.

Referring to FIGS. 1-4F, in one embodiment, the inner housing 20 of the biological fluid separation device 10 includes a dispenser assembly or dispenser unit 90 that allows the plasma 16 contained within a plasma collection channel 48 to be expelled in a precise, controlled, and efficient manner.

Referring to FIGS. 1-4F, in one embodiment, the inner housing 20 includes a plasma collection channel 48 between the plasma chamber outlet 46 and the outlet 32 of the inner housing 20. In this manner, after separation, the plasma 16 flows through the plasma chamber outlet 46 to the plasma collection channel 48. The plasma collection channel 48 allows the plasma 16 to be collected and stored within the inner housing 20, until it is desired to transfer the plasma 16 out of the inner housing 20.

In one embodiment, the plasma collection channel 48 has a serpentine shape. The diameter of the serpentine shape of the plasma collection channel 48 is sized to prevent bubbles from forming within the plasma 16 and to keep the plasma 16 flowing through the channel 48 in capillary form. The serpentine shape of the plasma collection channel 48 also allows for the length of the channel that the plasma 16 flows into to be increased while maintaining capillary form.

Referring to FIGS. 1-4F, in one embodiment, the inner housing 20 also includes a dispenser assembly or dispenser unit 90 that allows the plasma 16 contained within the plasma collection channel 48 to be expelled in a precise, controlled, and efficient manner. For example, once a sufficient amount of plasma 16 is collected within the plasma collection channel 48, the inner housing 20 can be removed from the outer housing 22, as shown in FIG. 4C. Next, the cap 80 is removed from the outlet 32, and the dispenser assembly 90 is used to dispense the plasma 16 from the plasma collection channel 48 of the inner housing 20, as shown in FIGS. 4D and 4E.

The dispenser assembly 90 of the inner housing 20 can include any dispenser structure that allows the plasma 16 to be expelled from the plasma collection channel 48 of the inner housing 20 in a precise, controlled, and efficient manner.

Referring to FIGS. 3C and 3D, one exemplary embodiment of the dispenser assembly 90 will be described. In one embodiment, the dispenser assembly 90 includes the plasma collection channel 48, the cap 80, the venting plug 82, a deformable portion 92, an air vent 96, and a one-way valve 98. In one embodiment, the deformable portion 92 includes a first dispenser bulb 93 and a second dispenser bulb 94.

In one embodiment, the cap 80 covers the outlet 32 and includes the venting plug 82 which allows air to pass therethrough and prevents the plasma portion 16 of the blood sample 12 from passing therethrough.

In one embodiment, the deformable portion 92 is transitionable between an initial position in which the plasma portion 16 is contained within the plasma collection channel 48 and a deformed position in which a portion of the plasma portion 16 is expelled from the plasma collection channel 48. Referring to FIGS. 4D and 4E, with the cap 80 removed from the outlet 32, and the deformable portion 92 transitioned to the deformed position, a portion of the plasma portion 16 is expelled from the biological fluid separation device 10, i.e., the plasma collection channel 48 of the inner housing 20. In one embodiment, the deformable portion 92 includes a first dispenser bulb 93 and a second dispenser bulb 94.

In use, when the deformable portion 92 is squeezed, air is pushed in the inner housing 20 to expel the plasma 16 out the plasma collection channel 48. In one embodiment, when the deformable portion 92 is squeezed, the air vent 96 on the deformable portion 92 is covered by a finger of a user to force air through one-way valve 98 to expel the plasma 16 out the plasma collection channel 48.

When the deformable portion 92 is released, the air vent 96 is no longer covered and air inflates the deformable portion 92 back up. Importantly, when the deformable portion 92 is released, the one-way valve 98 prevents plasma 16 from being pulled back into the plasma collection channel 48 after dispensing. In this manner, the dispensing assembly 90 of the present disclosure makes sure that the plasma 16 contained within the plasma collection channel 48 is only able to flow in one direction, i.e., out the plasma collection channel 48.

Referring to FIGS. 5-7D, in another exemplary embodiment, the plasma chamber outlet 46 of the inner housing 20 is in fluid communication with a portion of the interior 76 of the outer housing 22. In such an embodiment, the dispensing assembly 90 of the inner housing 20 of the embodiment discussed with reference to FIGS. 1-4F is removed, and plasma 16 is allowed to flow directly out the plasma chamber outlet 46 into a portion of the interior 76 of the outer housing 22.

Referring to FIG. 7A, in this embodiment, as a blood sample 12 is drawn within the inner housing 20, the plasma 16 is separated and exits the plasma chamber outlet 46 and collects in the outer housing 22. Referring to FIG. 7B, the discard cellular portion 14 of the blood sample 12 remains within the inner housing 20 and can be disposed of after separation of the plasma 16. Referring to FIGS. 7C and 7D, the plasma 16 contained within the outer housing 22 may then be manually transferred or presented directly to clinical analyzers.

In operation, plasma generation in the embodiment shown in FIGS. 1-4F, having a plasma collection unit or dispensing assembly 90 that allows for collection of the plasma 16 within the inner housing 20, is stopped when the inner housing 20 is filled.

The blood draw and plasma volume varies from patient to patient as more or less blood is required to fill the plasma collection unit. Removal of the plasma collection unit in the embodiment shown in FIGS. 5-7D allows additional plasma to be generated beyond the capacity of the collection unit. This gives the benefit of increased plasma volume (300-700 μL from 3 mL whole blood depending on patient hematocrit, versus, e.g., 150-250 μL as may be limited by a plasma collection unit). Another benefit of the embodiment shown in FIGS. 5-7D is that the plasma 16 sample can be presented directly to clinical analyzers or manually dispensed as dictated by workflow needs.

Figure 12A:
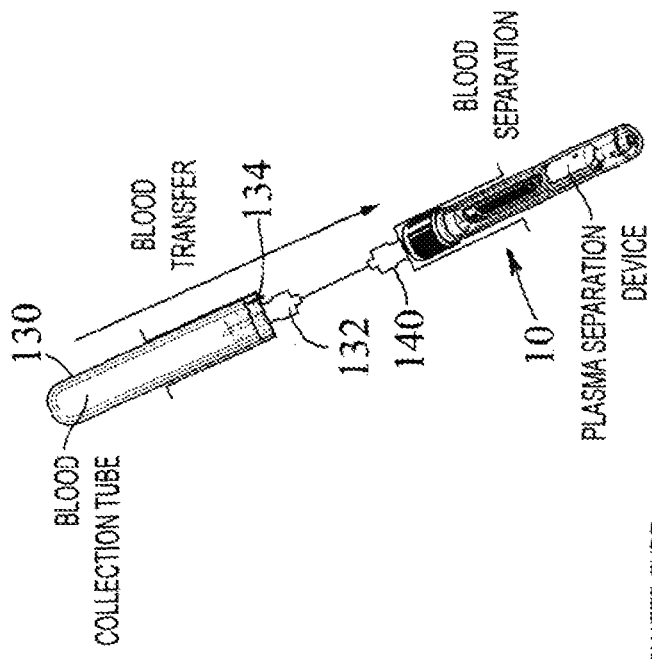
FIG. 12A is a perspective view of a first step of using a biological fluid separation device of the present disclosure in an indirect draw process in accordance with another embodiment of the present invention.
Figure 12B:
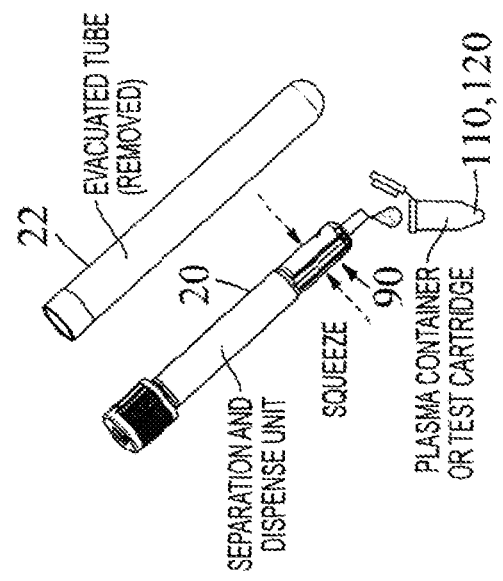
FIG. 12B is a perspective view of a second step of using a biological fluid separation device of the present disclosure in an indirect draw process in accordance with another embodiment of the present invention.
Figure 12C:
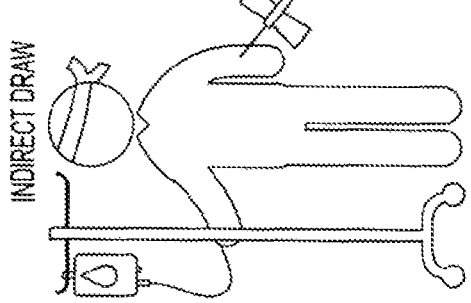
FIG. 12C is a perspective view of a third step of using a biological fluid separation device of the present disclosure in an indirect draw process in accordance with another embodiment of the present invention.
Figure 13:
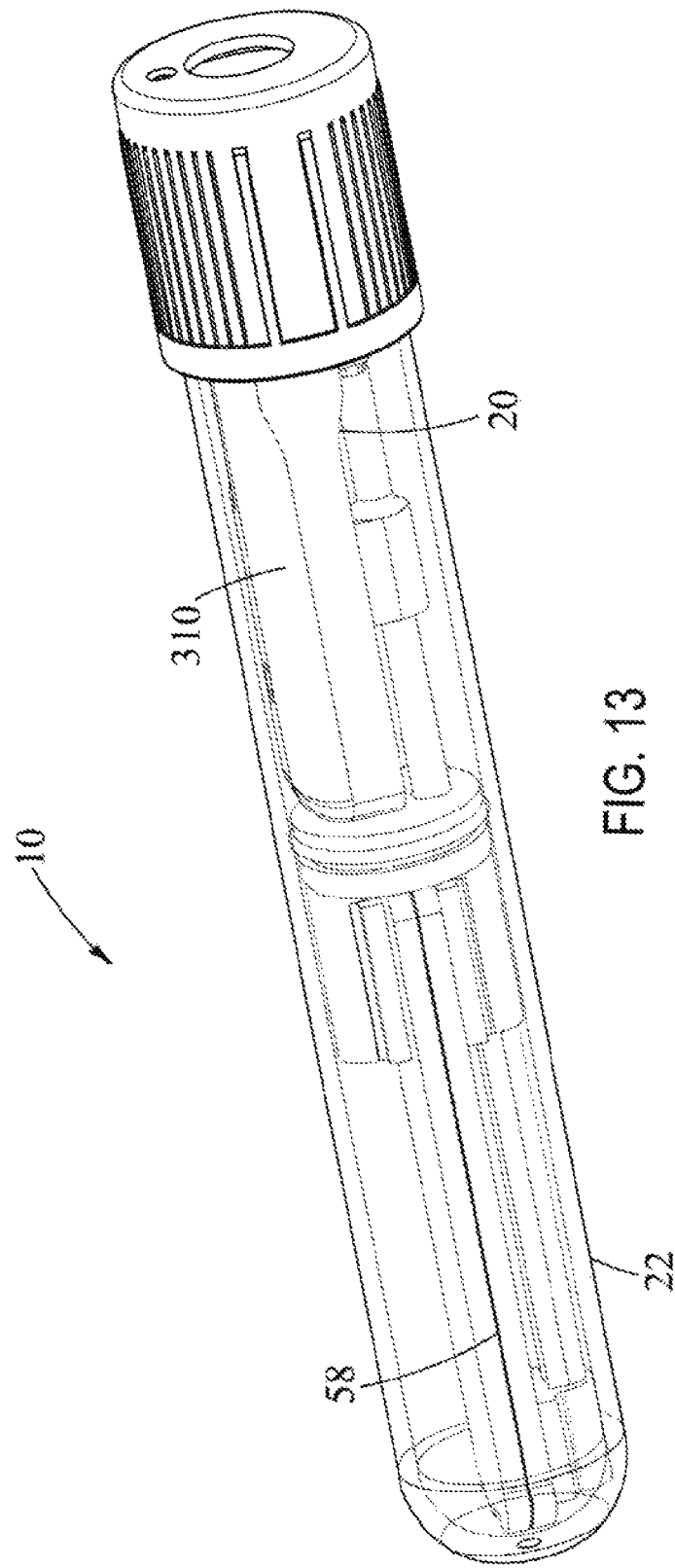
FIG. 13 is a perspective view of a biological fluid separation device in accordance with another embodiment of the present invention.
Figure 14:
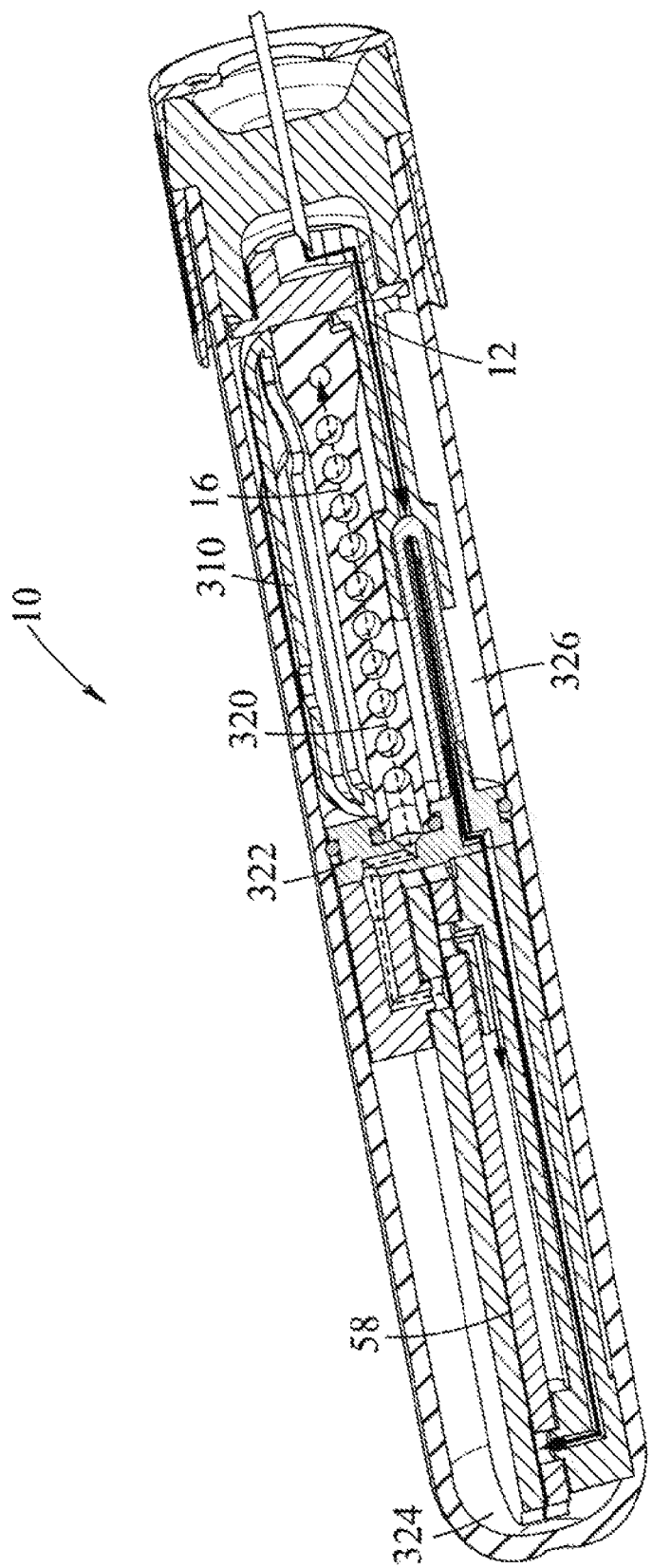
FIG. 14 is a cross-sectional view of FIG. 13 in accordance with another embodiment of the present invention.
Figure 15:
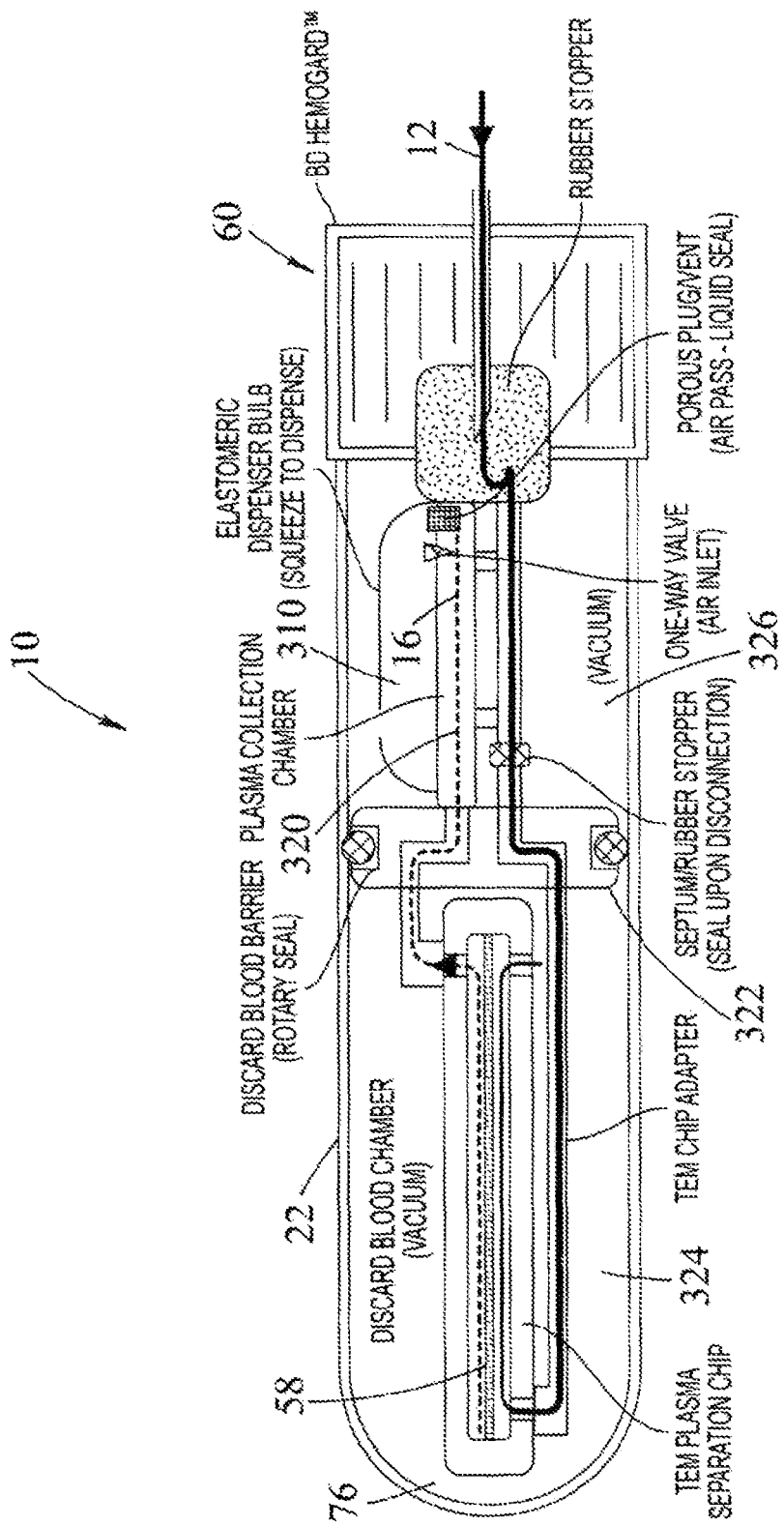
FIG. 15 is a cross-sectional view of FIG. 13 in accordance with another embodiment of the present invention.

In the embodiment shown in FIGS. 5-7D, the blood draw volume may increase to a flat 3 mL for all patients rather than varying between patients. Therefore, plasma separation time can increase in proportion with the increased blood draw volume. To mitigate the effect of increased run time, the embodiment shown in FIGS. 5-7D can be combined with the off-patient separation method, as shown in FIGS. 12A-12C, as described in more detail below.

Referring to FIGS. 8-10D, in another exemplary embodiment, the plasma chamber outlet 46 of the inner housing 20 is in fluid communication with a diagnostic assembly 200. In such an embodiment, the dispensing assembly 90 of the inner housing 20 of the embodiment discussed with reference to FIGS. 1-4F is removed, and plasma 16 is allowed to flow directly out the plasma chamber outlet 46 into the diagnostic assembly 200. In such an embodiment, the plasma 16 fills the diagnostic assembly 200 for immediately testing of the plasma 16 for analytes after separation, without a need to dispense any plasma 16 from the biological fluid separation device 10.

In one embodiment, the diagnostic assembly 200 includes a diagnostic interface 202 in communication with the plasma chamber outlet 46, a sensor 204 for testing the plasma portion 16 of the blood sample 12, and a venting plug 206 which allows air to pass therethrough and prevents the plasma portion 16 of the blood sample 12 from passing therethrough.

Referring to FIG. 10C, in one embodiment, the diagnostic assembly 200 includes a single sensor 204. Referring to FIG. 10C, in one embodiment, the diagnostic assembly 200 includes three sensors 204. Referring to FIG. 10C, in one embodiment, the diagnostic assembly 200 includes many sensors 204. The diagnostic assembly 200 may include any number of sensors 204 needed for a desired testing application.

In one embodiment, the venting plug 206 of the diagnostic assembly 200 allows a vacuum to pull plasma 16 into the diagnostic interface 202 and to fill the diagnostic assembly 200. For example, the venting plug 206 allows a vacuum 78 of the outer housing 22 to be in communication with the diagnostic assembly 200 to pull plasma 16 into the diagnostic assembly 200. The venting plug 206 allows air to pass through while preventing the plasma 16 of the blood sample 12 from passing through. For example, once the plasma 16 fills the diagnostic assembly 200, the venting plug 206 becomes saturated with blood and is wetted out. Once this happens, the diagnostic assembly 200 is filled with plasma 16 and no more plasma 16 is pulled into the diagnostic assembly 200. With the diagnostic assembly 200 fully filled with plasma 16 and the venting plug 206 wetted out, the diagnostic assembly 200 is also sealed.

Referring to FIGS. 8-10D, the diagnostic assembly 200 provides an on-board diagnostic unit for immediately testing the plasma 16 for analytes after separation. The diagnostic assembly 200 would utilize but not be limited to optical tests and other methods. The possible applications include qualitative "yes or no" tests for the presence of analytes, e.g., similar to common pregnancy tests, and quantitative results for analytes like cholesterol or sodium. Referring to FIG. 10B, in one embodiment, the on-board diagnostic assembly 200 could work alone. Referring to FIG. 10D, in one embodiment, the on-board diagnostic assembly 200 could interface with a test reader, for example, a diagnostic adapter 208, e.g., a cell phone adapter, which connects the device 10 to a point of care diagnostic instrument 210, e.g., a cell phone camera, for imaging and analysis of the sample results.

The diagnostic assembly 200 of the device 10 provides for efficient point-of-care workflow and clinician safety by eliminating the need to transfer the plasma 16 to a separate test cartridge. The diagnostic assembly 200 of the device 10 would also reduce the required volume of plasma 16 needed, e.g., in some embodiments, from ranges of 200-400 uL of plasma down to 10-50 uL, which would also reduce the run time of the device, e.g., in some embodiments, from 50-140 seconds down to 15-30 seconds, and required blood volume, e.g., in some embodiments, from 1-3 mL down to 0.2-0.5 mL.

Referring to FIGS. 4A-4F, use of a biological fluid separation device 10 of the present disclosure will now be described. Advantageously, a biological fluid separation device 10 of the present disclosure allows for a variety of different ways to collect and separate a plasma portion of a blood sample. For example, in one embodiment, a biological fluid separation device 10 of the present disclosure can be used with a conventional tube holder 102 having a cannula or non-patient needle 100 in a direct draw process as described in more detail below. In another embodiment, a biological fluid separation device 10 of the present disclosure can be used with a separate blood collection tube 130 in an indirect draw process as described in more detail below.

Figure 4B:
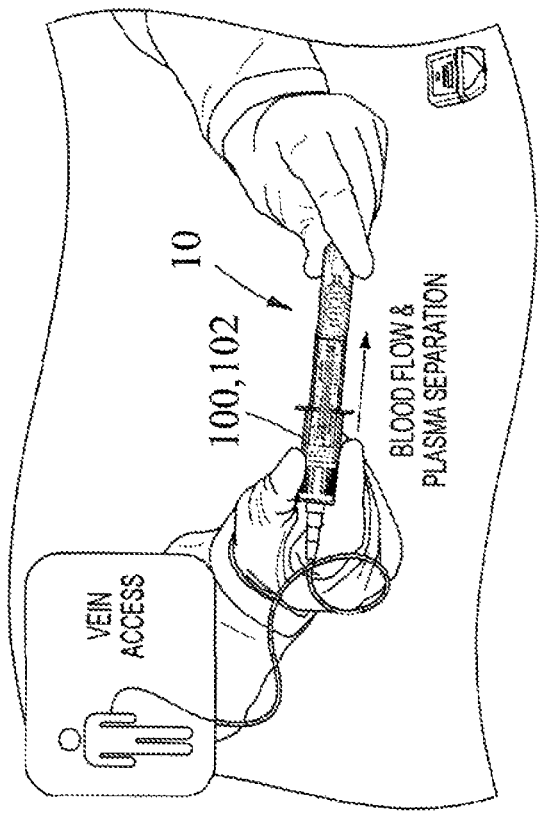
FIG. 4B is a perspective view of a second step of using a biological fluid separation device of the present disclosure in accordance with an embodiment of the present invention.
Figure 4A:
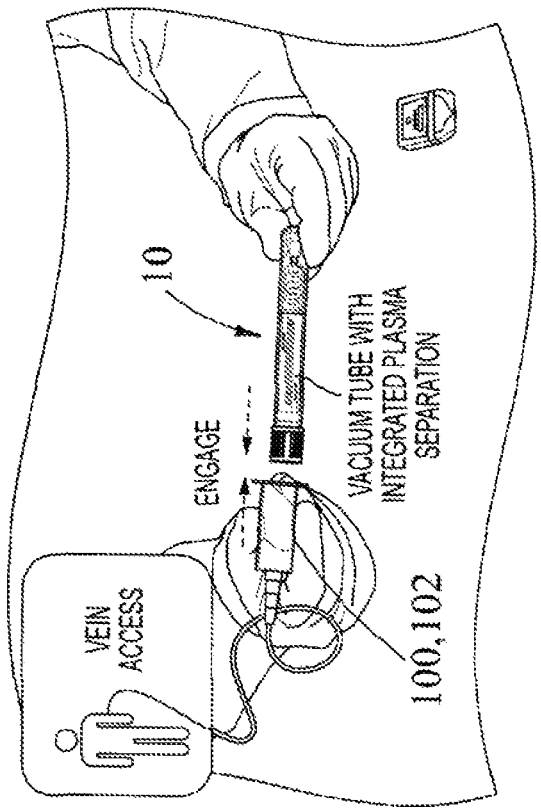
FIG. 4A is a perspective view of a first step of using a biological fluid separation device of the present disclosure in accordance with an embodiment of the present invention.
Figure 4F:
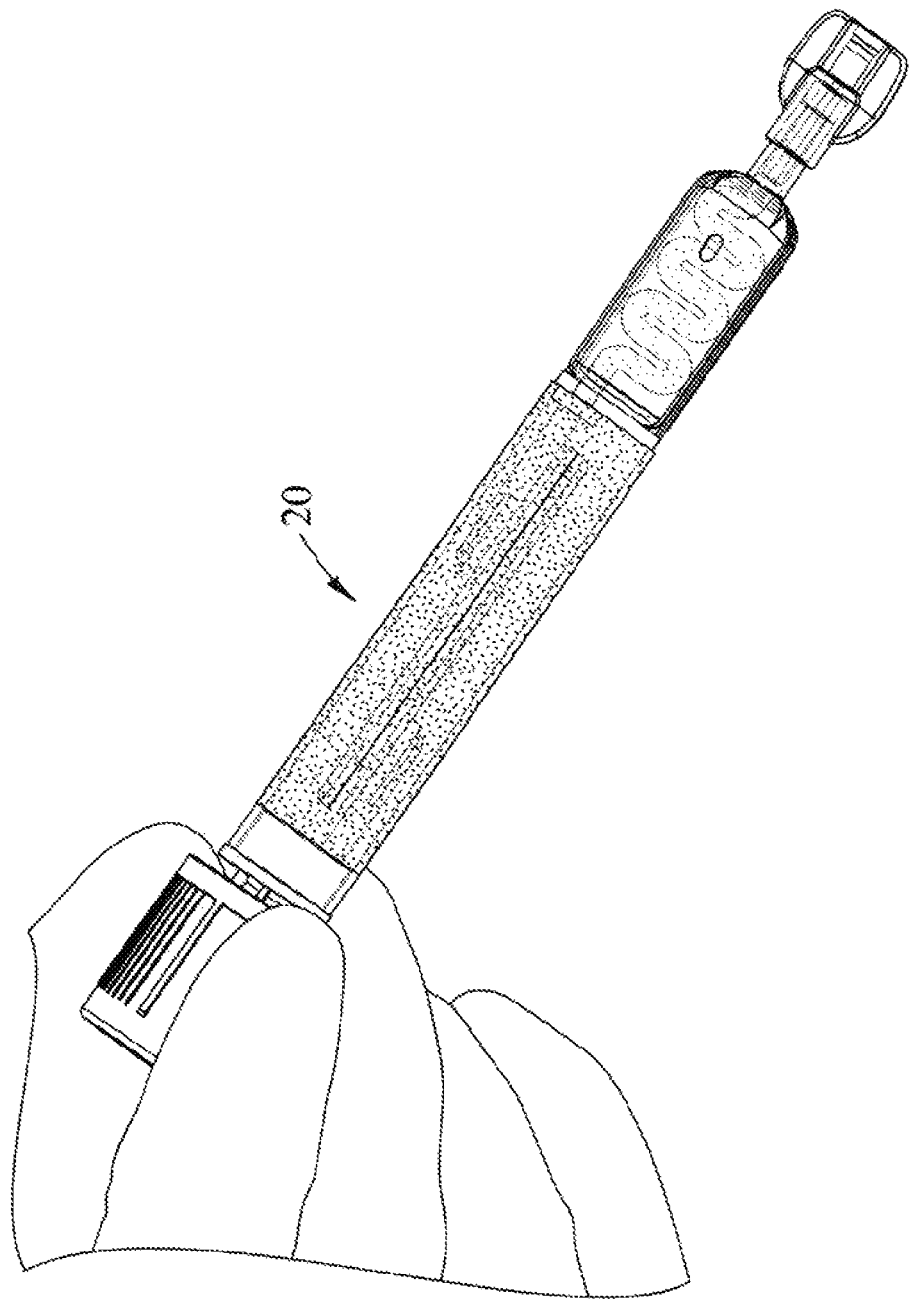
FIG. 4F is a perspective view of an inner housing of a biological fluid separation device in accordance with an embodiment of the present invention.
Figure 5:
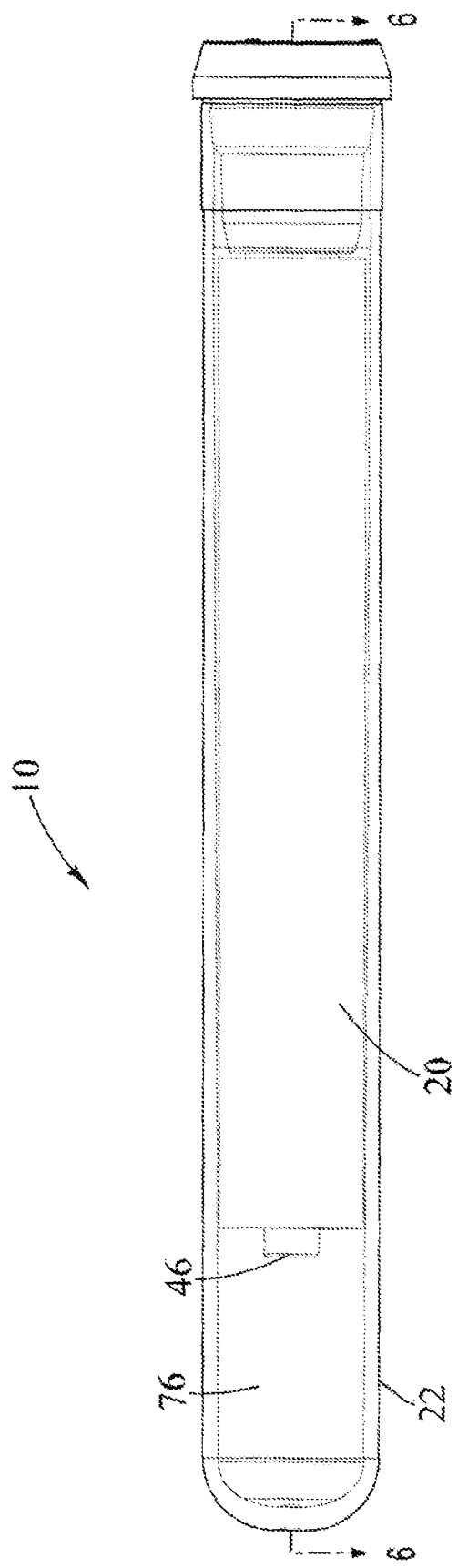
FIG. 5 is a perspective view of a biological fluid separation device in accordance with another embodiment of the present invention.
Figure 6:
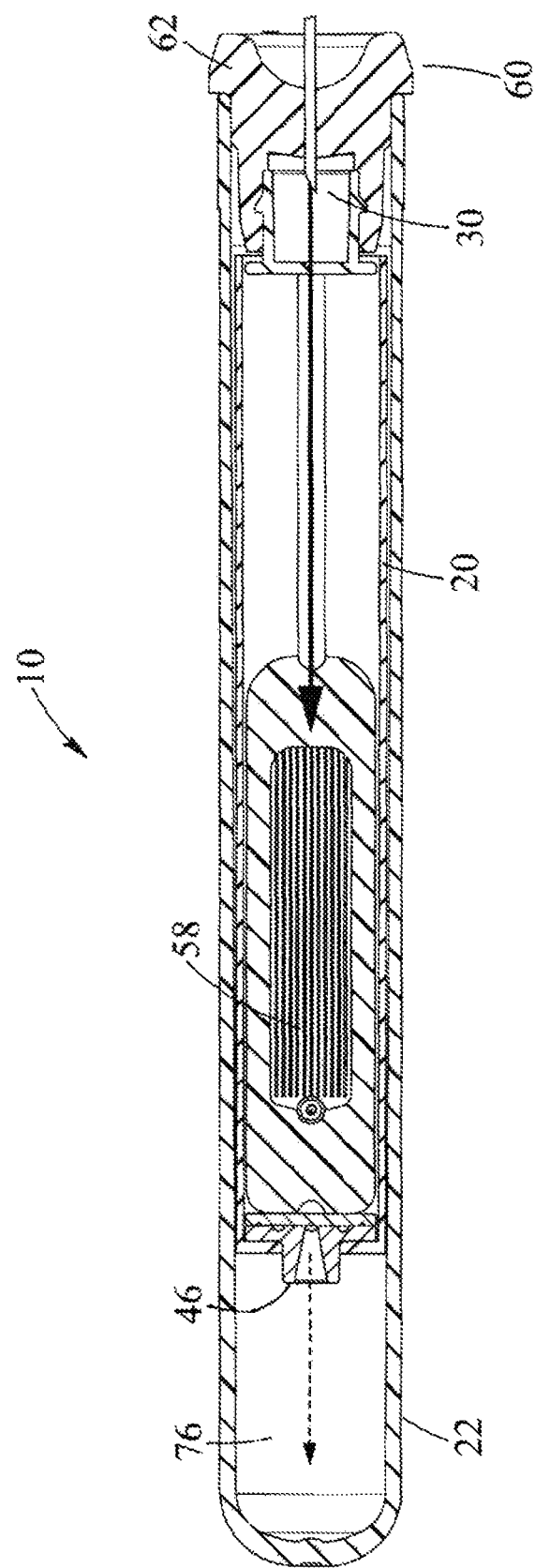
FIG. 6 is a cross-sectional view taken along line 6-6 of FIG. 5 in accordance with another embodiment of the present invention.
Figure 7:
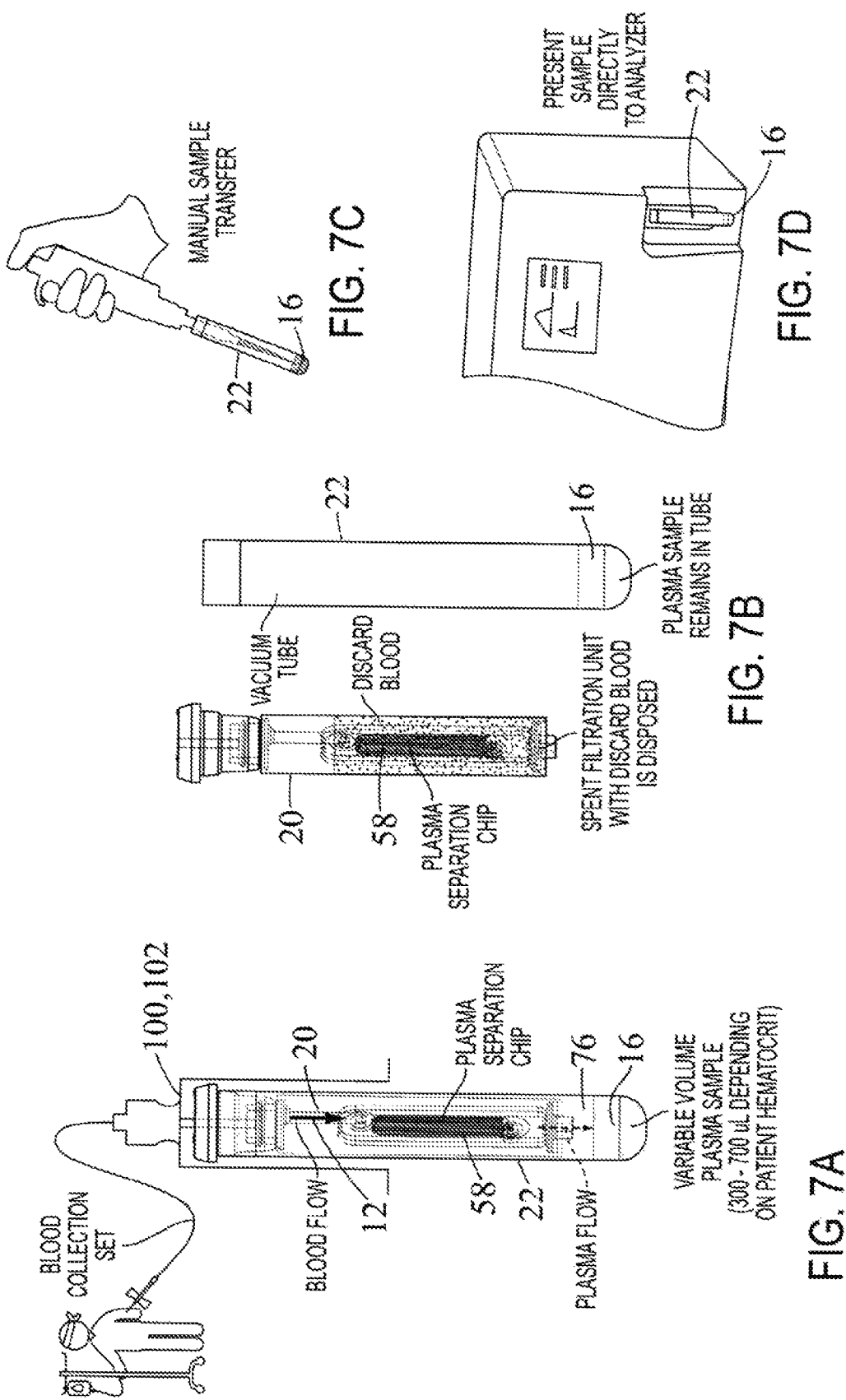
FIG. 7A is a perspective view of a first step of using a biological fluid separation device of the present disclosure in accordance with another embodiment of the present invention.
FIG. 7B is a perspective view of a second step of using a biological fluid separation device of the present disclosure in accordance with another embodiment of the present invention.
FIG. 7C is a perspective view of a dispensing step of using a biological fluid separation device of the present disclosure in accordance with another embodiment of the present invention.
FIG. 7D is a perspective view of a dispensing step of using a biological fluid separation device of the present disclosure in accordance with another embodiment of the present invention.
Figure 8:
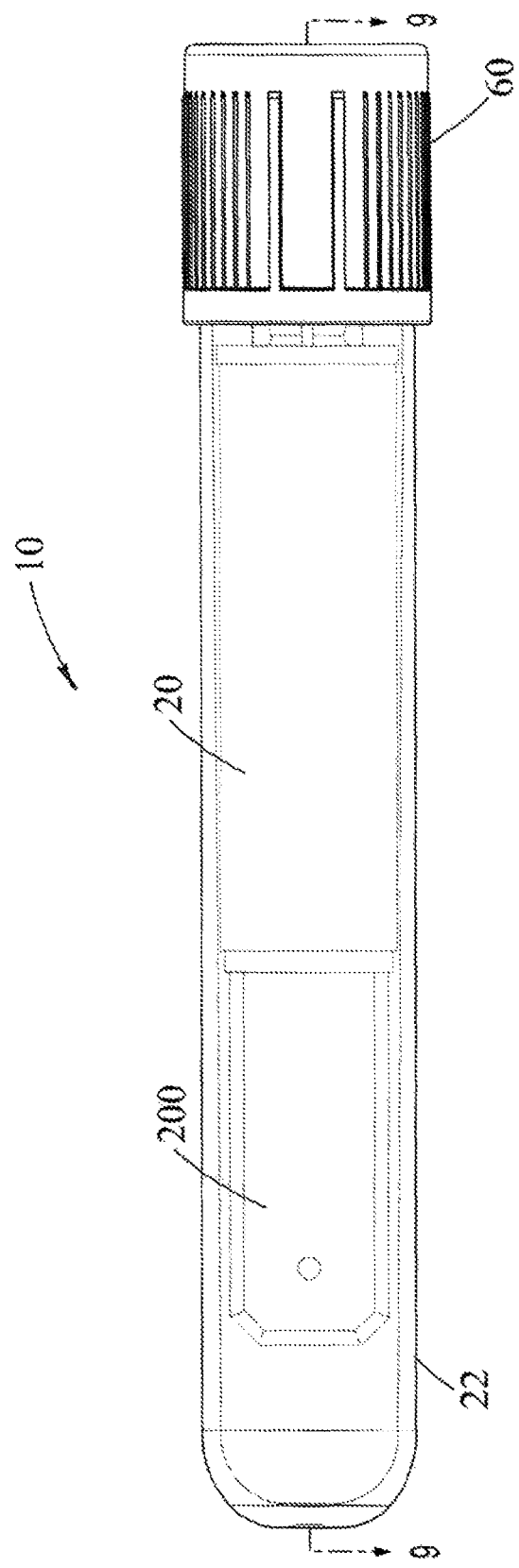
FIG. 8 is a perspective view of a biological fluid separation device in accordance with another embodiment of the present invention.
Figure 9:
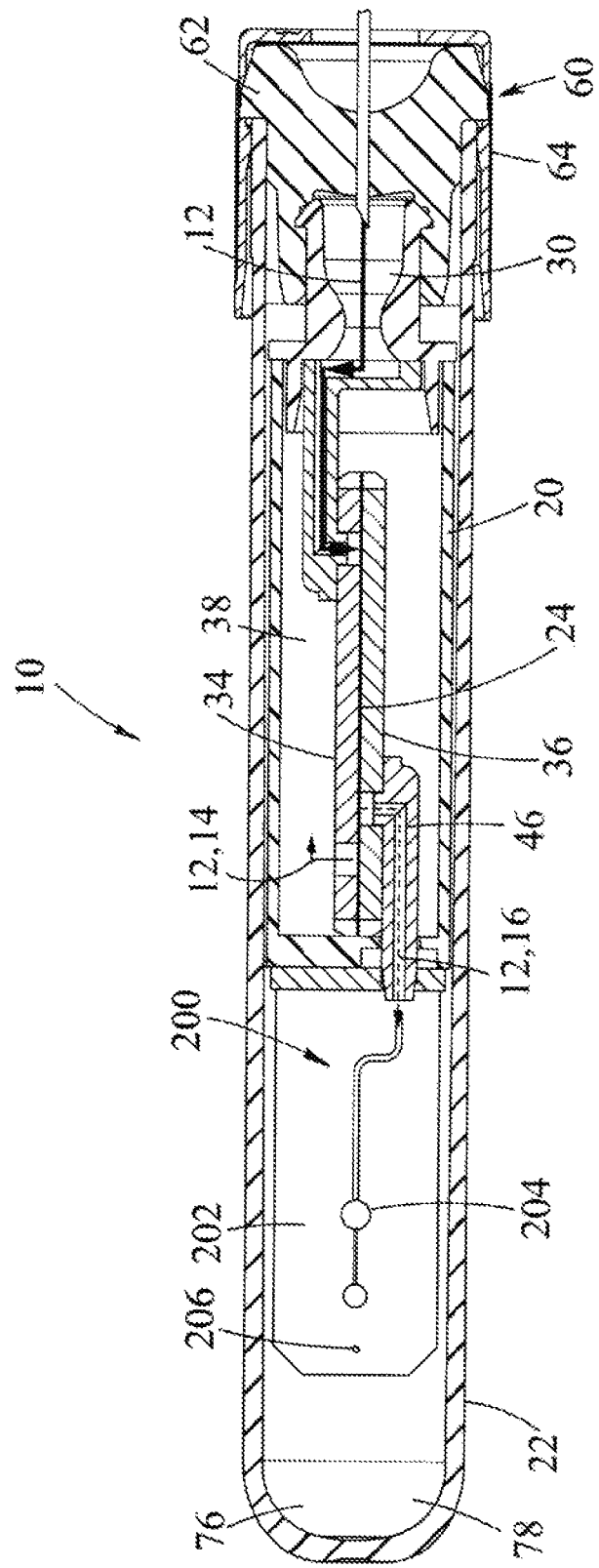
FIG. 9 is a cross-sectional view taken along line 9-9 of FIG. 8 in accordance with another embodiment of the present invention.
Figure 11B:
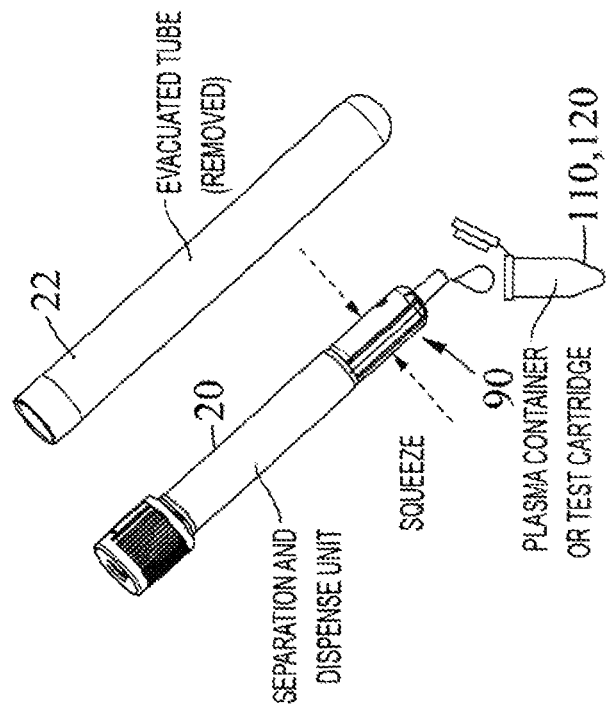
FIG. 11B is a perspective view of a second step of using a biological fluid separation device of the present disclosure in a direct draw process in accordance with another embodiment of the present invention.
Figure 11A:
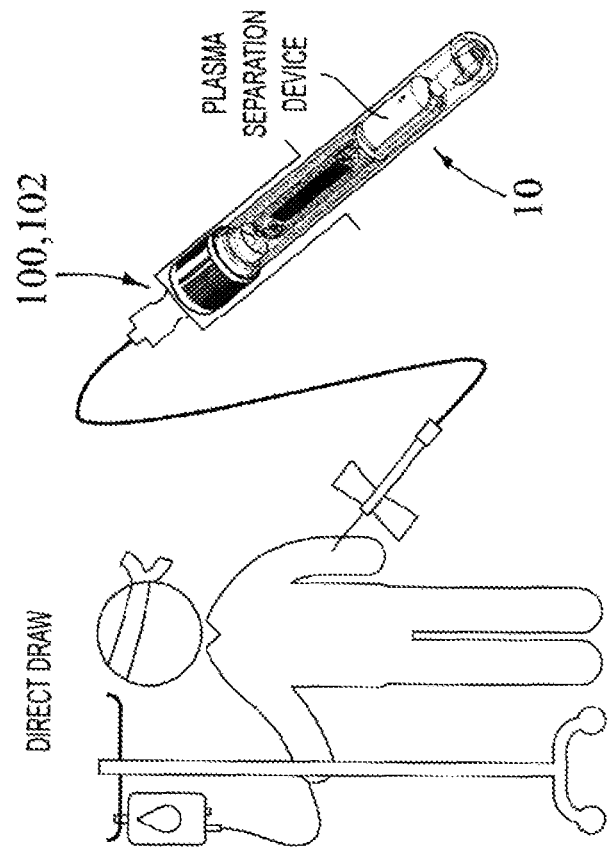
FIG. 11A is a perspective view of a first step of using a biological fluid separation device of the present disclosure in a direct draw process in accordance with another embodiment of the present invention.

Referring to FIGS. 4A, 4B, and 11A, use of a biological fluid separation device 10 of the present disclosure with a conventional tube holder 102 having a cannula or non-patient needle 100 in a direct draw process will now be discussed. A biological fluid separation device 10 of the present disclosure is compatible with conventional blood collection sets, e.g., a tube holder 102 or other conventional blood collection devices.

In use, a needle cannula or non-patient needle 100 (FIGS. 2 and 4A) is inserted directly into the blood chamber 34 of the inner housing 20 of the biological fluid separation device 10 through the pierceable self-sealing stopper 62 of closure 60. As shown in FIGS. 4A and 4B, the biological fluid separation device 10 including the combined inner housing 20 and the outer housing 22 may be inserted into a conventional tube holder 102 having a cannula or non-patient needle 100 through which biological fluid, such as a blood sample 12, is passed.

Next, with the biological fluid separation device 10 of the present disclosure directly connected with the tube holder 102, a blood sample 12 is pulled into the blood chamber 34 of the inner housing 20 of the biological fluid separation device 10 from the conventional tube holder 102 by the draw of the first vacuum 78 contained in the outer housing 22 and the second vacuum 38 contained in the inner housing 20. For example, when the non-patient needle 100 of the tube holder 102 pierces the stopper 62 of the closure 60, the first vacuum 78 contained in the outer housing 22 and the second vacuum 38 contained in the inner housing 20 draw the blood sample 12 within the blood chamber 34 of the inner housing 20 via the non-patient needle 100 of the tube holder 102.

The venting plug 82 and/or the venting plug valve 84 allow air to pass through while preventing the blood sample 12 and/or plasma portion 16 from passing through. Once the blood sample 12 fills the separator chip 58, the first vacuum 78 and the second vacuum 38 are no longer in communication and begin acting separately. The second vacuum 38 continues discarding the cellular portion 14 of the blood sample 12 from the blood chamber outlet 42 to the blood discard chamber 45. Furthermore, the first vacuum 78 continues drawing the plasma portion 16 through the separator 24 into the plasma chamber 36. Once the plasma portion 16 fills the plasma chamber 45 and reaches the venting plug 82 the venting plug will become saturated with blood and wetted out, ending separation. If the desired operation requires it, the first vacuum 78 and second vacuum 38 can be connected by a venting plug valve 84 which allows air to pass between the first vacuum 78 and second vacuum 38 but prevents blood sample 12 from reaching the outer housing 22.

Thus, in one embodiment, the first vacuum 78 and the second vacuum 38 initially act together as a single vacuum while the first vacuum 78 and the second vacuum 38 are in communication theretogether. Next, after the separator chip 58 is filled with blood sample 12, the first vacuum 78 and the second vacuum 38 are no longer in communication together and act separately. In another embodiment, the first vacuum 78 and second vacuum 38 are kept in communication for the duration of operation by a venting plug valve 84.

Once the blood sample 12 is collected and a desired amount of plasma 16 is separated, the biological fluid separation device 10 is removed from the tube holder 102. Next, the separated plasma 16 is ready to be dispensed and/or analyzed as described in further detail below.

Referring to FIGS. 12A-12C, use of a biological fluid separation device 10 of the present disclosure with a separate blood collection tube 130 in an indirect draw process will now be discussed.

The indirect draw process allows for off-patient separation of plasma. Referring to FIG. 12A, in this embodiment, a blood sample 12 is collected in a conventional blood collection tube 130 in a conventional blood collection procedure. Blood collection using a conventional blood collection tube 130 allows a blood sample 12 to be collected from a patient faster. In this manner, the time that a patient is required to go through a blood collection procedure is reduced.

Next, referring to FIG. 12B, the blood collection tube 130 containing a blood sample 12 is then connected to the biological fluid separation device 10 for separation of the plasma 16 of the blood sample 12. In this manner, separation of the plasma 16 using the biological fluid separation device 10 occurs while no blood collection devices are connected to a patient.

Referring to FIG. 12B, in one embodiment, the biological fluid separation device 10 includes a biological fluid separation device connector 140 removably connectable to a connector 132 of a blood collection tube 130. This connection provides a sealed, secure connection between the biological fluid separation device 10 and the blood collection tube 130 during separation of plasma 16 using the biological fluid separation device 10.

In one embodiment, the blood collection tube 130 includes an air vent 134. The air vent 134 allows for air to be released to allow a vacuum within the biological fluid separation device 10 to pull the blood sample 12 into the biological fluid separation device 10 and draw the plasma portion 16 through the separator 24 into the plasma chamber 36.

Once a desired amount of plasma 16 is separated, the biological fluid separation device 10 is removed from the blood collection tube 130. Next, the separated plasma 16 is ready to be dispensed and/or analyzed as described in further detail below.

With the separated plasma 16 collected in the biological fluid separation device 10, the separated plasma 16 is ready to be dispensed and/or analyzed. In one embodiment, the dispenser assembly 90 of the biological fluid separation device 10 may be used. For example, referring to FIGS.

1-4F, in one embodiment, the inner housing 20 of the biological fluid separation device 10 includes a dispenser assembly or dispenser unit 90 that allows the plasma 16 contained within a plasma collection channel 48 to be expelled in a precise, controlled, and efficient manner.

Referring to FIG. 4C, in such an embodiment, once plasma separation and collection is complete, the inner housing 20 is separated from the outer housing 22 (FIG. 4C). In one embodiment, the inner housing 20 is separated from the outer housing 22 by removing the closure 60, which is still attached to the inner housing 20, from the outer housing 22. Removal of the closure 60 may be accomplished by the user grasping both the outer shield 64 of the closure 60 and the outer housing 22 and pulling or twisting them in opposite directions.

Once the inner housing 20 is separated from the outer housing 22, the cap 80 may then be removed from the inner housing 20 exposing the outlet 32 of the inner housing 20. Removal may be accomplished by the user grasping an exterior portion of the cap 80 and pulling the cap 80 from the inner housing 20. In one embodiment, the plasma 16 is held within the plasma collection channel 48 of the inner housing 20 by capillary action after removal of the cap 80.

Referring to FIGS. 4D, 4E, 11B, and 12C, the plasma 16 may then be dispensed from the plasma collection channel 48 of the inner housing 20 by activation of a dispensing assembly 90. As described above, in one embodiment, the inner housing 20 also includes a dispenser assembly 90 that allows the plasma 16 contained within the plasma collection channel 48 to be expelled in a precise, controlled, and efficient manner. For example, referring to FIG. 4C, once a sufficient amount of plasma 16 is collected within the plasma collection channel 48, the inner housing 20 can be removed from the outer housing 22. Next, the cap 80 is removed from the outlet 32, and the dispenser assembly 90 is used to dispense the plasma 16 from the plasma collection channel 48 of the inner housing 20.

Referring to FIG. 4D, in one embodiment, the plasma 16 may be transferred to a sample container 110, while minimizing the exposure of the medical practitioner to the plasma 16 of the blood sample 12.

Referring to FIG. 4E, in one embodiment, the plasma 16 may be transferred to a device intended to analyze the plasma 16, e.g., such as a point-of-care testing device 120, a cartridge tester, or a near patient testing device, while minimizing the exposure of the medical practitioner to the plasma 16 of the blood sample 12.

After plasma 16 separation, the separated plasma 16 is ready to be dispensed and/or analyzed. In one embodiment, the embodiment of the biological fluid separation device 10 shown in FIGS. 5-7D may be used. For example, referring to FIGS. 5-7D, in another embodiment, the plasma chamber outlet 46 of the inner housing 20 is in fluid communication with a portion of the interior 76 of the outer housing 22. In such an embodiment, the dispensing assembly 90 of the inner housing 20 of the embodiment discussed with reference to FIGS. 1-4F is removed, and plasma 16 is allowed to flow directly out the plasma chamber outlet 46 into a portion of the interior 76 of the outer housing 22.

Referring to FIG. 7B, in such an embodiment, once plasma separation and collection is complete, the inner housing 20 is separated from the outer housing 22. Referring to FIG. 7B, the discard cellular portion 14 of the blood sample 12 remains within the inner housing 20 and can be disposed of after separation of the plasma 16. Referring to FIGS. 7C and 7D, the plasma 16 contained within the outer housing 22 may then be manually transferred or presented directly to clinical analyzers.

In one embodiment, the separated plasma 16 fills a diagnostic assembly 200 for immediate testing of the plasma 16 for analytes after separation, without a need to dispense any plasma 16 from the biological fluid separation device 10. For example, referring to FIGS. 8-10D, the diagnostic assembly 200 provides an on-board diagnostic unit for immediately testing the plasma 16 for analytes after separation. The diagnostic assembly 200 would utilize but not be limited to optical tests and other methods. The possible applications include qualitative "yes or no" tests for the presence of analytes, e.g., similar to common pregnancy tests, and quantitative results for analytes like cholesterol or sodium. Referring to FIG. 10B, in one embodiment, the on-board diagnostic assembly 200 could work alone. Referring to FIG. 10D, in one embodiment, the on-board diagnostic assembly 200 could interface with a test reader, for example a diagnostic adapter 208, e.g., a cell phone adapter, which connects the device 10 to a point of care diagnostic instrument 210, e.g., a cell phone camera, for imaging and analysis of the sample results.

Referring to FIGS. 13-17C, in other embodiments, the blood chamber outlet 42 (FIG. 3E) is in fluid communication with a portion of the interior 76 of the outer housing 22.

Referring to FIGS. 17A-17C, in one embodiment, the device 10 directs the discard blood or cells 14 into the bottom of the interior 76 of the outer housing 22 during plasma separation. The plasma 16 is collected into a dispenser unit or dispenser assembly 310 that is removably connectable to a portion of the outer housing 22. Referring to FIG. 17B, in one embodiment, the dispenser unit 310 is removed with the closure 60. The separation chip 58 and discard blood or cells 14 remain in the outer housing 22 and are discarded. Referring to FIG. 17C, in one embodiment, the plasma 16 can then be dispensed for testing using the dispenser unit 310.

Referring to FIGS. 13-16C, in one embodiment, the device 10 includes a plasma collection channel 320 extending from the plasma chamber outlet 46 into a portion of the dispenser unit 310. Referring to FIGS. 15-17C, in one embodiment, the device 10 includes a stopper 322 that is sized relative to the interior 76 of the outer housing 22 to provide sealing engagement with the sidewall 74 of the outer housing 22. In one embodiment, the stopper 322 divides the interior 76 of the outer housing 22 into a first sealed portion 324 and a second portion 326. In one embodiment, the blood chamber outlet 42 is in fluid communication with the first sealed portion 324 of the interior 76 of the outer housing 22.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A biological fluid separation device adapted to receive a blood sample having a first portion and a second portion, the biological fluid separation device comprising:
    a housing having an inlet and an outlet and a venting plug having a porosity;

a blood chamber having a blood chamber inlet and a blood chamber outlet, the blood chamber adapted to receive the blood sample;
a separated chamber having a chamber outlet;
a separator disposed between the blood chamber and the separated chamber, the separator adapted to trap the first portion in the blood chamber and allow the second portion to pass through the separator into the separated chamber; and
an outer housing removably connectable to the housing,
wherein the outer housing contains a first vacuum and the housing contains a second vacuum,
wherein, with the housing connected to the outer housing, the housing is disposed within the outer housing,
wherein the first vacuum and the second vacuum are in communication via the venting plug, and
wherein the porosity of the venting plug allows air to pass therethrough to the outer housing and prevents the second portion of the blood sample from passing therethrough to the outer housing.

2. The biological fluid separation device of claim 1, wherein the first portion is a cellular portion, and the second portion is a plasma portion.

3. The biological fluid separation device of claim 2, wherein the first vacuum and the second vacuum draw the blood sample within the housing and draw the plasma portion through the separator into the separated chamber.

4. The biological fluid separation device of claim 1, wherein the separator comprises a membrane surface having pores.

5. The biological fluid separation device of claim 1, wherein the separator comprises a track-etched membrane.

6. The biological fluid separation device of claim 1, further comprising a closure covering the inlet, and
wherein, with the housing connected to the outer housing, the closure seals the open end of the housing.

7. The biological fluid separation device of claim 1, wherein the inlet of the housing is at a first end and the outlet of the housing is at an opposite second end.

8. The biological fluid separation device of claim 1, further comprising a plasma collection channel between the chamber outlet and the outlet of the housing.

9. The biological fluid separation device of claim 8, wherein the plasma collection channel has a serpentine shape.

10. The biological fluid separation device of claim 1, further comprising a dispenser assembly comprising:
a cap covering the outlet and including the venting plug; and
a deformable portion transitionable between an initial position in which the second portion is contained within the separated chamber and a deformed position in which a portion of the second portion is expelled from the separated chamber.

11. The biological fluid separation device of claim 10, wherein, with the cap removed from the outlet, and the deformable portion transitioned to the deformed position, a portion of the second portion is expelled from the biological fluid separation device.

12. The biological fluid separation device of claim 1, further comprising a diagnostic assembly comprising:
a diagnostic interface in communication with the chamber outlet of the separated chamber; and
a sensor for testing the second portion.

13. A biological fluid separation device adapted to receive a blood sample having a cellular portion and a plasma portion, the biological fluid separation device comprising:
an inner housing having an inlet and an outlet and a venting plug having a porosity;
a blood chamber having a blood chamber inlet and a blood chamber outlet, the blood chamber receives the blood sample;
a plasma chamber having a plasma chamber outlet;
a separator disposed between the blood chamber and the plasma chamber, the separator adapted to trap the cellular portion in the blood chamber and allow the plasma portion to pass through the separator into the plasma chamber; and
an outer housing removably connectable to the inner housing,
wherein, with the inner housing connected to the outer housing, the inner housing is disposed within the outer housing, and wherein a vacuum is defined by at least one of the inner housing and the outer housing to draw the plasma portion of the blood sample through the separator, and
wherein the porosity of the venting plug allows air to pass therethrough to the outer housing and prevents the plasma portion of the blood sample from passing therethrough to the outer housing.

14. The biological fluid separation device of claim 13, further comprising a biological fluid separation device connector removably connectable to a connector of a blood collection tube.

15. The biological fluid separation device of claim 13, wherein the outer housing comprises an evacuated tube.

16. A biological fluid separation device adapted to receive a blood sample having a cellular portion and a plasma portion, the biological fluid separation device comprising:
an outer housing having an open end, a closed end, and a sidewall extending therebetween and defining an interior;
a dispenser unit removably connectable to the outer housing, the dispenser unit comprising a venting plug having a porosity; and
an inner housing within the outer housing, the inner housing comprising:
a blood chamber having a blood chamber inlet and a blood chamber outlet, the blood chamber receives the blood sample, the blood chamber outlet in fluid communication with a portion of the interior of the outer housing;
a plasma chamber having a plasma chamber outlet;
a separator disposed between the blood chamber and the plasma chamber, the separator adapted to trap the cellular portion in the blood chamber and allow the plasma portion to pass through the separator into the plasma chamber; and
a plasma collection channel extending from the plasma chamber outlet into the dispenser unit,
wherein the porosity of the venting plug allows air to pass therethrough to the outer housing and prevents the plasma portion of the blood sample from passing therethrough to the outer housing.

17. The biological fluid separation device of claim 16, further comprising a stopper sized relative to the interior of the outer housing to provide sealing engagement with the sidewall of the outer housing.

18. The biological fluid separation device of claim 17, wherein the stopper divides the interior of the outer housing into a first sealed portion and a second portion.

19. The biological fluid separation device of claim 16, wherein, with the dispenser unit disconnected from the outer housing, the plasma portion is contained within the dispenser unit.

* * * * *